(12) United States Patent
Norling et al.

(10) Patent No.: US 9,222,867 B2
(45) Date of Patent: Dec. 29, 2015

(54) RESONANT MICROMACHINED BIOCHEMICAL SENSOR

(76) Inventors: Brian L. Norling, Santa Barbara, CA (US); John C. G. Dunfield, Palm Desert, CA (US)

( * ) Notice: Subject to any disclaimer, the term of this patent is extended or adjusted under 35 U.S.C. 154(b) by 207 days.

(21) Appl. No.: 13/476,989

(22) Filed: May 21, 2012

(65) Prior Publication Data

US 2014/0031263 A1  Jan. 30, 2014

Related U.S. Application Data

(63) Continuation-in-part of application No. 13/344,614, filed on Jan. 5, 2012, now abandoned.

(60) Provisional application No. 61/460,694, filed on Jan. 5, 2011.

(51) Int. Cl.
| | |
|---|---|
| G01R 33/00 | (2006.01) |
| G01R 33/34 | (2006.01) |
| G01N 5/02 | (2006.01) |
| G01R 33/028 | (2006.01) |
| G01N 1/40 | (2006.01) |
| G01R 33/12 | (2006.01) |
| G01N 1/22 | (2006.01) |

(52) U.S. Cl.
CPC .................. *G01N 5/02* (2013.01); *G01N 1/405* (2013.01); *G01R 33/0286* (2013.01); *G01R 33/1261* (2013.01); *G01N 2001/2223* (2013.01)

(58) Field of Classification Search
CPC .................................................. G01R 33/0286

USPC .............. 73/19.01, 19.03, 23.2, 24.01–24.06; 422/50, 68.1, 69, 83, 88, 98

See application file for complete search history.

(56) References Cited

U.S. PATENT DOCUMENTS

| | | |
|---|---|---|
| 3,561,253 A | 2/1971 | Dorman |
| 5,162,691 A | 11/1992 | Mariani |
| 5,719,324 A | 2/1998 | Thundat |
| 5,856,722 A | 1/1999 | Haronian |
| 6,289,717 B1 | 9/2001 | Thundat |

(Continued)

OTHER PUBLICATIONS

Domanski, K., et al. "Fabrication and properties of piezoresistive cantilever beam with porous silicon element." Journal of Vacuum Science & Technology B 21.1 (2002): 48-52.*

(Continued)

*Primary Examiner* — Lyle Alexander
*Assistant Examiner* — Robert Eom
(74) *Attorney, Agent, or Firm* — Guy Cumberbatch

(57) ABSTRACT

A sensor system is formed from a micro machined resonant structure with multiple resonant elements, a tracking resonator control electronics, and signal processing algorithms. The moving elements of the resonator are coated with chemically active materials that change mass when exposed to the target chemical resulting in a change in frequency or period of oscillation. The changes in frequency or period are processed by multi-sensor chemical detection algorithms to identify chemical types and concentrations. In essence, the resonator and drive electronics form a closed loop oscillator operating at the resonator's natural frequency. The resonators are formed from silicon using photolithographic processes. The resonator design includes in-plane resonant motion combined with dynamic balance to operate with a high Q even in the presence of atmospheric pressure.

23 Claims, 23 Drawing Sheets

(56) References Cited

U.S. PATENT DOCUMENTS

| | | |
|---|---|---|
| 6,820,469 B1 * | 11/2004 | Adkins et al. ............... 73/54.25 |
| 6,933,164 B2 | 8/2005 | Kubena |
| 7,089,813 B2 | 8/2006 | Takeuchi |
| 7,171,844 B2 | 2/2007 | Cunningham |
| 7,458,265 B2 | 12/2008 | Shih |
| 7,942,056 B2 | 5/2011 | Mutharasan |
| 7,959,873 B1 | 6/2011 | Roukes |
| 8,136,385 B2 | 3/2012 | Adams |
| 8,220,067 B2 | 7/2012 | Adams |
| 2006/0188399 A1 * | 8/2006 | Smid .......................... 422/82.02 |
| 2007/0119232 A1 * | 5/2007 | Konno et al. ............... 73/24.01 |
| 2010/0186507 A1 * | 7/2010 | Gunthner ............. G01C 19/574 73/504.14 |

OTHER PUBLICATIONS

Lee, Dongkyu, et al. "Microcantilevers with nanowells as moisture sensors."Sensors and Actuators B: Chemical 137.2 (2009): 561-565.*

Lee, Jungchul, and William P. King. "Microthermogravimetry using a microcantilever hot plate with integrated temperature-compensated piezoresistive strain sensors."Review of scientific instruments 79.5 (2008): 054901.*

* cited by examiner

RESONANT MICROMACHINED BIOCHEMICAL SENSOR

CROSS-REFERENCE TO RELATED APPLICATIONS

This application is a continuation-in-part of U.S. application Ser. No. 13/344,614, filed Jan. 5, 2012 now abandoned, which claims priority to U.S. Provisional Patent Application Ser. No. 61/460,694, filed on Jan. 5, 2011, the disclosure of which is incorporated by reference herein in its entirety.

FIELD OF THE INVENTION

The present invention relates to chemical sensors, including biosensors, used in trace chemical detection, explosives detection, chemical hazard detection and biological hazard detection.

BACKGROUND OF THE INVENTION

Sensors for detecting explosives typically employ cantilever resonators driven by electrostatic forces or electromagnetic forces and capacitive pickoff. These sensors typically operate by flowing the sample volumes of air over the sensors directly over the resonant cantilever. These motional displacements of the cantilever sensor designs have several shortcomings. First, the cantilever sensors displace prodigious amounts of gas relative to their size because the cantilever is thin and flat relative to the direction of motion. At atmospheric pressure, this would result in a very low Q, the measure of energy consumed per cycle versus the energy stored per cycle. Where narrow gaps are used between the resonating cantilever and the electrostatic drive, sense electrode, squeeze film damping becomes very significant. Even at pressures wherein the mean free path of the gases is on the order of the gap, the effect on Q is significant. The Q of the resonator is a primary indicator of the detection threshold of the resonator. The higher the Q, the better the sensitivity of the resonator.

Additionally, the direct impingement of the sample air flow on the sensor surface has the degrading factor of potentially collecting particulate contamination of the mass-spring-damper system. Particulate contamination commonly imparts a frequency shift error well in excess of the vapor detection level.

The resonant cantilever described in U.S. Pat. No. 7,521,257 detects chemical species by the change in amplitude of resonance. This approach suffers from inaccuracies due to changes in Q or pressure. The teeter-totter resonator described in U.S. Pat. No. 6,820,469 operates with motion out of plane that displaces a sizeable volume of gas each cycle resulting with a relatively low Q. The electromagnetically driven resonator described in U.S. Pat. No. 6,668,627 utilizes a thin flat plate moving out of plane resulting in displacement of a large amount of gas per cycle resulting in a low Q. The resonant plate approach described in U.S. Pat. No. 7,305,883 also utilizes out of plane motion resulting in a sub-optimal Q. Patents 2005/0101026 A, WO/2008/005096, and 2009/0246881 A1 teach about optical detection methods without the properties of mass change for gravimetric sensing.

SUMMARY OF THE INVENTION

The present application provides a biochemical sensing platform of the "gravimetric" sensor technology class. Gravimetric sensors detect chemicals and biological agents based upon the change in mass of the specific captured material. In this embodiment, an in-plane resonant structure is excited at controlled amplitude and becomes the defining element of a closed loop controlled oscillator.

A high flow volume air handling system is used to collect and concentrate the target chemical. This system includes an electrostatic particulate collection grid system along with vapor collection system using coatings with affinity for the target chemical. Sample measurement is performed in a separate chamber to control particulate contamination. The grid is heated to release the chemical vapors from the particles and coatings. These vapors flow over the motional masses of the resonant sensors.

In the preferred embodiment, a resonant sensor system comprises a resonant sensor element with a driven resonant sensing mode along the thin plane of the motional mass, typically the plane of the wafer, to minimize damping losses thereby maximizing Q. This resonant sensor element employs two motional masses that are dynamically balanced to reduce energy loss to the support structure. A linkage constraining the two motional masses of the sensor may be included to constrain the opposing resonant element to move 180 degrees out of phase with each other.

On the motional mass, coatings are applied which have high specificity for capturing or reacting with the target chemical compound to affect a change in resonant frequency. The motional mass has holes to increase its surface area-to-mass ratio and thereby increase detection sensitivity.

The sensor system includes conductive traces across the moving element oriented substantially orthogonal to the driven resonant motion and with a magnetic field substantially orthogonal to the conductive traces and the vector of resonant motion. This provides a drive force to sustain resonant amplitude by running current through the drive conductive traces and employs separate conductive traces to measure the back EMF signals for sense detection that are essentially in phase with the driven coils.

Drive electronics control the amplitude of the driven resonant mode at approximately its natural frequency using a phase-locked-loop and a proportional-integration-differential (PID) control loop. It is important to note that the drive is adding energy at the resonant frequency of the same magnitude as the losses in the mechanical system. Therefore, the system resonates at the damped natural frequency. A signal processing system detects a change in resonant frequency or period and converts this to an indication of target chemical detection.

The proposed technology has inherent advantages that distinguish it from prior technologies:
- The core technology is proven to detect mass changes with unprecedented accuracy
- The in-plane resonance is very high Q for high accuracy, low noise and low power
- The use of a reference resonator provides rejection of errors common to all sensors
- The electromagnetic drive and sense provides extremely low noise performance
- The electromagnetic drive does not have high electric fields, avoiding electrostatic particle attraction as is inherent in electrostatic drive systems
- Simultaneous analysis of multiple agents in single samples
- Low false positive rate due to digital signal processing of multiple signals and redundancy
- Single platform provides ability to sense multiple chemical compounds
- Low cost, robust, low power and re-useable for man portability and remote operation Near real time results and advantages in early warning due to low detection threshold Physical separation of the collection/concentration and test/analysis processes greatly reduces particulate contamination and non-specific binding of contaminants.

Common analysis platform for biological and chemical agents

Design can be mechanized for use in the rugged, handheld, portable, battery-powered applications.

MEMS sensors can be manufactured in high volume at low cost.

The technology is fundamentally less expensive, smaller, lighter, and lower power than ion mobility spectrometers.

BRIEF DESCRIPTION OF THE DRAWINGS

The invention will now be explained and other advantages and features will appear with reference to the accompanying schematic drawings wherein.

DETAILED DESCRIPTION OF THE PREFERRED EMBODIMENTS

Figure 1:
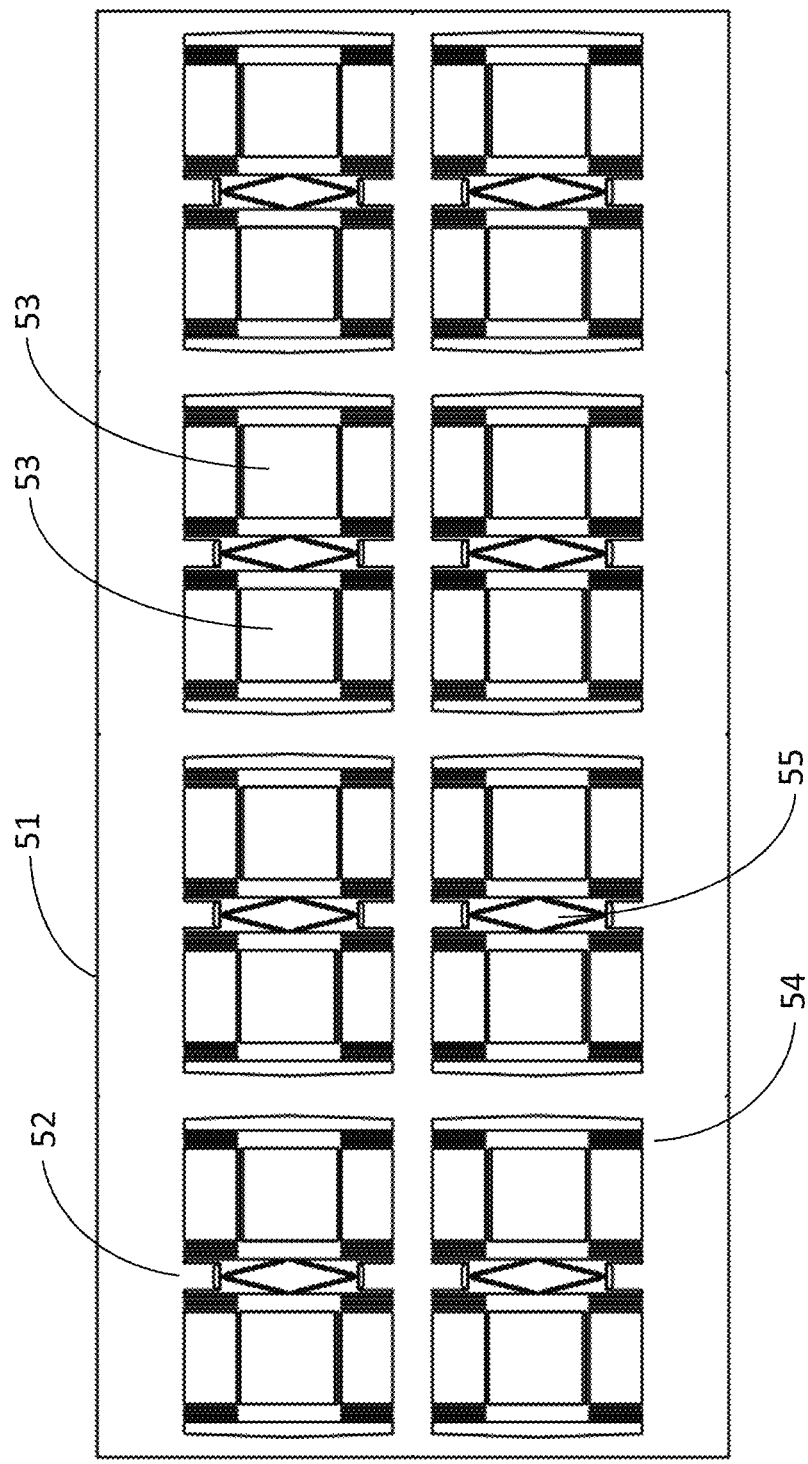
FIG. 1 is an illustration of the sensor array with eight sensors.

The present application is a sensing system for detection of chemicals, biological compounds, and other potential items which impart a change of mass. At the heart of the system is a spring-mass-damper mechanical system that is maintained at resonance by electronics at its damped natural frequency. When the mass of the spring-mass system changes, the frequency of the system changes. This change in frequency is the essential signal for biochemical detection. The advantage of measuring frequency change is the ability to achieve accuracy of measurement orders of magnitude better than analog-to-digital convertor technology. Additionally, the signal processing is virtually all-digital with the inherent stability of digital signal processing.

The chemical sample collection/concentration system also has the advantage of capturing both particulate and vapor target chemicals. This is a significant advantage because some chemicals, such as explosives, have low vapor pressures and also have an affinity to attach to particles. By collecting and heating particles, significant vapors can be released to increase sensing capability of the system. This collection/concentration system with particle capture capability also has the advantage of keeping the particles from contacting the spring-mass-damper sensor system, thereby avoiding the potential error the mass of a particle would generate.

The key elements of the inventions are listed in the table below and the details and novelty of these elements are defined in the following sections.

System Design
Sensor Element Design
Sensor Array Design
Sensor Manufacturing
Sensor Coating Application
Sample Collection and Concentration Technology
Electronics Design
Signal Processing (Analog, Digital)
System Integration, Calibration and Test
User Interface System Design:

The system is an integration of Micro Electromechanical Systems (MEMS) sensors ("resonant sensors" or "resonators"), analog electronics, digital electronics, air handling system elements and related packaging. The analog electronics provide electromagnetic drive current to sustain the resonant amplitude. They also amplify the velocity signal from the sensor, employing state-of-the-art low noise amplifiers. Digital electronics perform the signal processing and system control signals. The man-machine interface and sample processing state machine are also one of the functions of the digital electronics.

The sensor (or resonator) detects a change in resonant frequency resulting from a change in mass defined nominally by the function $\Delta F = (K/(M_0 + \Delta M))^{0.5}$ where F=frequency, K=stiffness of the resonant structure of the driven mode, $M_0$=motional mass of the resonant structure, and $\Delta M$=change in mass of detected material. The resonant surface is coated with a compound which reacts with specificity to the desired substance or substance class to be detected. This could be a biological or chemical agent which creates a change in mass. When the sampling medium e.g. air or liquid sample contains the target material or agent, it interacts with the coating and generates a change in mass which is detected by a frequency measurement on the active sensor and no change on a neutral coated sensor or detectable change in other sensors in the array. The interaction is detected primarily as a difference frequency or period measurement change between resonators. The present invention creates an improved detection system for biological agents and chemical compounds. It can be used in a laboratory environment or can be deployed in the field. It is simple to operate, and responds to low threat concentration levels for early detection. The heart of the system is an array of MEMS-based resonant sensing elements with the capability to detect agent induced changes in mass on the order of $10^{-15}$ grams with high precision. This novel MEMS resonant structure array is inherently shock hardened for ruggedness and also to facilitate multiple means of sensor delivery.

The present resonator array embodiment has eight sensing elements. Preferably, up to seven are coated with different active chemical compounds allowing for the simultaneous analysis of multiple agents in a single sample and one is the passive reference resonator. The use of an identical non-chemically-reactive reference resonator provides insensitivity to common mode errors such as contamination, aging, moisture absorption, and temperature. Multiple chemical compounds can be used in the sensor array to aid in discrimination for reduced false positive errors. Use of more than one sensor with identical active coatings can also be used to "vote" on the presence of a threat chemical response. It may also be optimal in some cases to detect the "contaminant" chemicals capable of producing false positive indications to reduce false positive probability.

The data acquisition system uses digital counters to determine frequency with extremely high accuracy and stability. This all digital approach is much lower power, higher resolution and higher stability than A-to-D based systems. This digital counter system is able to achieve high resolution by using a high frequency reference clock as a vernier to accurately resolve the phase of the output frequency of the resonator. The primary signal sensitivity is the difference frequency through a period measurement between the active resonators and the reference resonator during the measurement interval. This difference in period provides common mode rejection of many potential error sources such as temperature sensitivity, clock aging, and moisture absorption.

The period of the active and reference resonators are processed by digital algorithms designed to remove residual sensitivities such as temperature and humidity.

The system can be configured in a multitude of embodiments as known to those skilled in the state of the art. The system level design controls the sample collection, sample concentration, sample processing, sensing algorithm processing, graphical user interface and communication. This invention is very small sized, low power, rugged, and mass producible at low cost due to MEMS/nano technology. The selection of open architecture allows for easy integrated with orthogonal sensing techniques.

A preferred embodiment of the system includes the following major components:

- A sensor array for detecting target chemicals materials
- An air handling system including a fan, ducting, and an electrostatic air cleaner for passing large volumes of sample air over the collection concentration grid to capture both vapor and particulate matter.
- A sample collection/concentration grid for capturing particles and absorbing target vapors.
- A vacuum chamber and pump for use in releasing the concentrated sample into a very small volume containing the sensor array and for pulling a vacuum to increase sensor Q for enhanced performance.
- Sensor control electronics to drive the resonant sensors and to control the sample system processing ("drive electronics").
- A digital electronics board to perform sensor sampling and to run detection algorithms.
- A case with user interface.

In a preferred embodiment a coarse filter is used to clean large particulate contamination from the high volume air flow channel. This cleaned air then flows across a pre-concentrator used to collect and concentrate the chemical particulate and vapor laden sample. This is especially effective in the chemicals having a low vapor pressure which adhere to particles. In this case, the chemical laden particles are collected and then the chemical vapor is released by bring them in close proximity to the sensor which could involve pressure differencing techniques or by heating the concentrated particles. In another embodiment, the system functions by filtering out the large particles and flowing the air through the high surface area array of holes in the sensor. Note that the airflow is turned off during the sample measurement process to reduce noise. The target chemical agent in the airflow reacts with a specific surface coating on the surface of the resonator to create a mass change.

It is also beneficial to add a Global Positioning System (GPS) to add position information to the chemical detection information. The locations traversed during sample collection can be tied to the sample data of this same location. The information can add value to the ability to locate the source of the biochemical emissions. It is also of value for keeping track of the location of sample collection point when the sample processing time lag results in significant location change.

Figure 2:
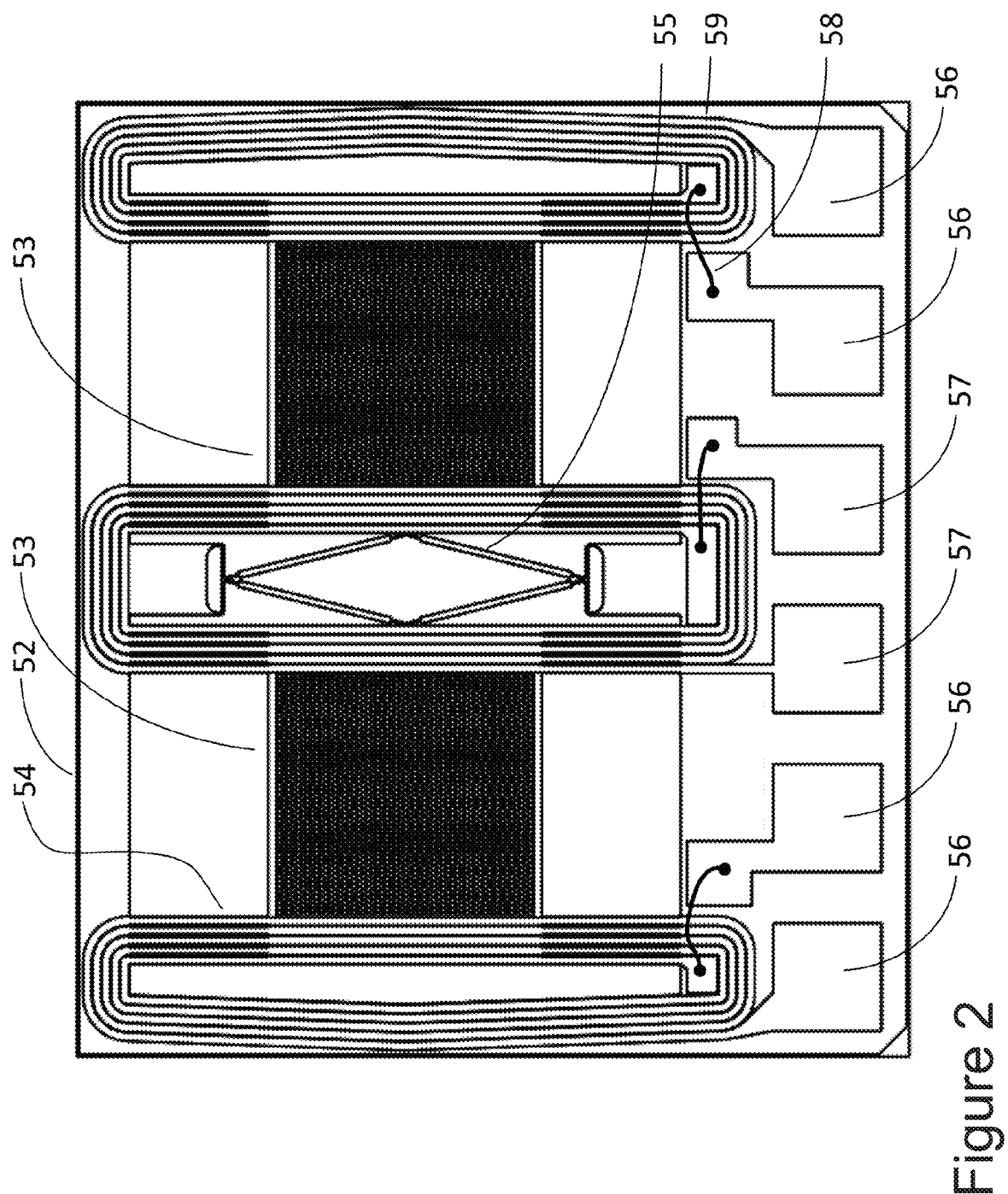
FIG. 2 is an illustration of the plan view of a single resonant sensor element.

Sensor Element Design:

Overview:

The use of an eight MEMS sensor array, shown as item 51 in FIG. 1, provides low cost, low power and high performance. The key elements of the sensor are shown in FIG. 2. Item 52 is an individual sensor. Item 53 is the detection grid. Item 4 are the suspension legs. These suspension legs are in the form of flexures. As will be seen, the flexures 4 suspend and constrain a motional mass to a resonant mode substantially in a plane. Flexures are defined as mechanical supports with a length substantially longer than the stiffness and its height substantially greater than its thickness. This geometry results in a suspension element with stiffness in one or two directions to be substantially different than the stiffness of the other directions. This ability is used to control the mode shapes of the sensor. Item 5 is the linkage that controls motion of the two halves of the sensor, constraining the desired resonant motion to move 180 degrees out of phase. Items 56 are the wire bond pads for the drive traces. Item 57 are the velocity sensing wire bond pads. Item 58 is the conductor loop wire bond jumper. Item 59 is the drive conductor loop. Each resonator operates as a free running oscillator with the resonant frequency controlled by the extraordinarily stable mass and stiffness properties of single crystal silicon with low doping levels. The driven resonator motion is in the plane of the wafer for low damping, resulting in an extremely high Q mechanical system. High Q enables low power and high frequency stability.

Figure 3:
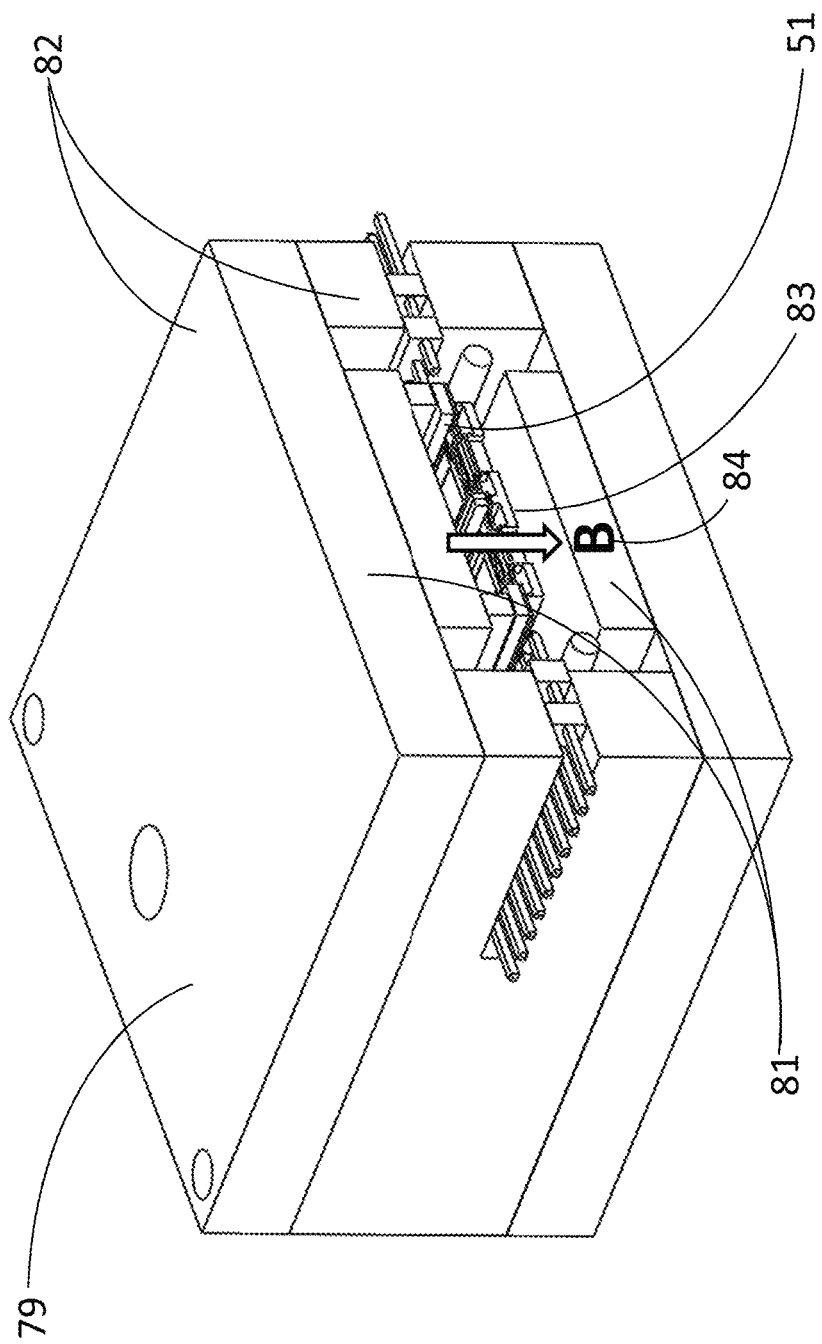
FIG. 3 is a cutaway illustration of the sensor in the magnetic field generated by permanent magnets and a magnetic return path.

The sensor is placed in a magnetic field with flux lines passing perpendicularly through the plane of the sensor as shown in FIG. 3. The oscillator loop operates by measuring the velocity of the resonator as a back EMF on the multiple loop gold conductors shown as item 59 in FIGS. 2 and 5. This signal level is amplified and compared to a precision reference such as a band gap voltage reference to control amplitude. Current is driven through an identical set of conductors on the opposite side of the resonator at the correct phase angle to accurately maintain control velocity. The advantage of this system is that it is extremely low noise. All of the noise contributions (including Brownian motion noise, Johnson noise, shot noise, amplifier voltage noise, and amplifier current noise) were optimized for low frequency jitter. The result is a threshold of detection at $10^{-15}$ grams.

The core MEMS sensing and oscillator technology have been developed and proven in the MEMS Precision Technology, Inc laboratory. The collection plate of the sensor Item 55 of FIGS. 4 and 5) can be either a flat plate structure or can be perforated with holes to vastly increase reactive surface area as shown in FIG. 5. Item 60 of FIG. 5 shows the hexagonal hole design which achieves near optimal surface area to volume ratio in a rigid structure. An opening is cut in the back side handle wafer to allow air to flow through the detector section. The sensor is inherently rugged and supports the environment of hand-held devices, vehicles and most remote delivery systems.

Dynamic Balance:

A preferred embodiment uses a two-piece dynamically balanced resonator. Dynamic balancing of the motional masses to reduces energy loss to the support structure in order to maximize sensor Q.

Figure 4:
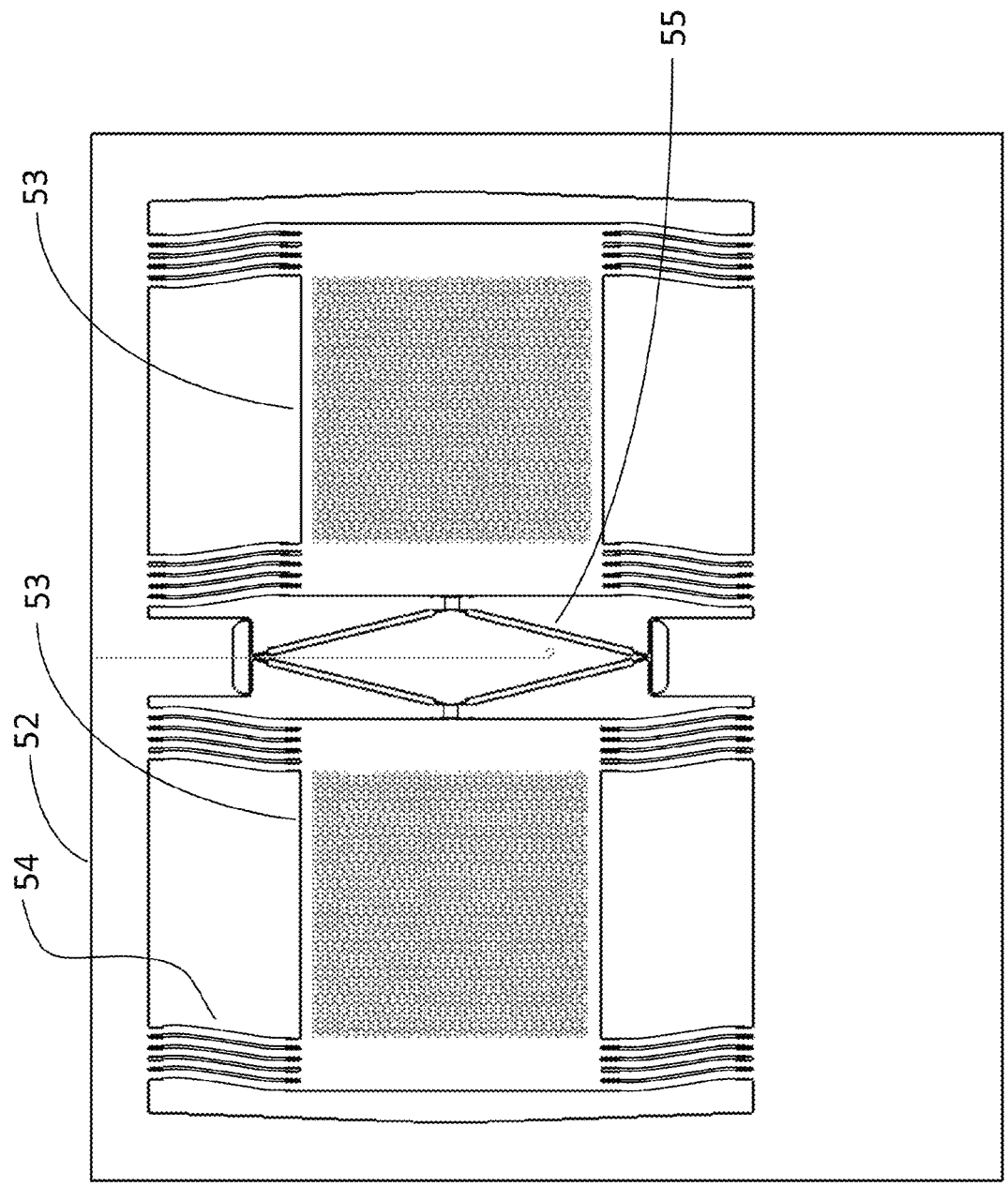
FIG. 4 is an illustration of the sensor driven resonant mode.
Figure 5:
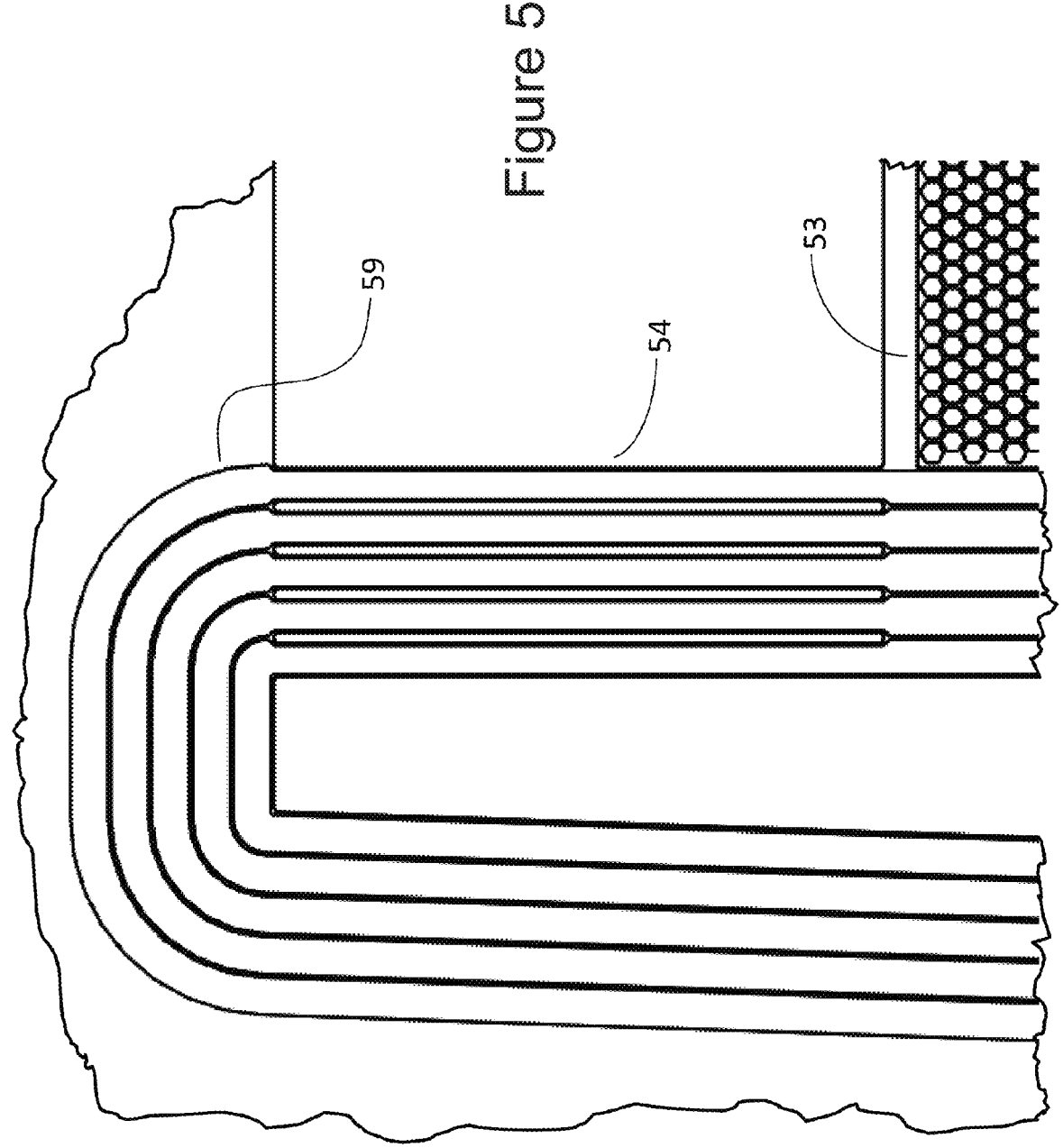
FIG. 5(4) is a cutaway illustration of suspension legs that support the motional mass.

A preferred embodiment drives the first resonant mode as shown in FIG. 4. This in-plane mode with large clearances to surrounding structure provides the lowest possible damping losses in the presence of gas. It is a design goal to ensure that every reaction has an equal and opposite reaction within the resonant structure. This is accomplished by designing a resonator suspension system which precisely matches the linear motion of the center-of-gravity and the mass of each half of the resonator. Additionally, even the small rotational motions each half of the sensor is made to cancel. The sub-micron accuracy of MEMS processing is also advantageous to achieving these dynamic balance goals. It is important to note that the diamond linkage, item 55, controls the resonant motion to be 180 degrees out of phase and minimizes sensitivity to shock and vibration.

Suspension, in-Plane Motion:

A suspension structure is an essential part of this design. It provides the spring in the spring-mass-damper resonant system. The suspension also defines the freedom of motion for the driven resonance and controls the frequency and mode shape of all other spurious resonant modes.

The resonator employs in-plane resonant motion to achieve maximum Q with clearances to stationary MEMS structure large relative to the motion to minimize squeeze film damping effects. The present invention has a much higher Q and is more accurate than surface micro-machined resonant cantilever beams resonating out of plane.

The suspension desirably comprises a thin planar structure, and thin flat beams are the preferred design. This causes the undesirable resonant modes in all directions to be substantially higher than the desired in-plane resonant mode. This reduces vibration sensitivity and increases ruggedness. It is often preferred to have multiple thin beams than a single thick beam. This can greatly reduce the stiffness of the desired operating resonant mode while keeping the resonant frequency of the undesirable modes high. It also allows metallization conductor traces separately across each beam.

As will be explained, the thin planar structure forming the suspension comprises two parts: a motional mass and an active coating on or in the motional mass. A set of springs preferably comprising flexures suspends and constrains the motional mass to a resonant mode in the plane of the thin planar structure. The coating has an affinity to capturing or reacting with the target chemical compound in order to change its own mass in response to the presence of the chemical compound and affect a change in the damped natural frequency of the thin planar structure.

Figure 6:
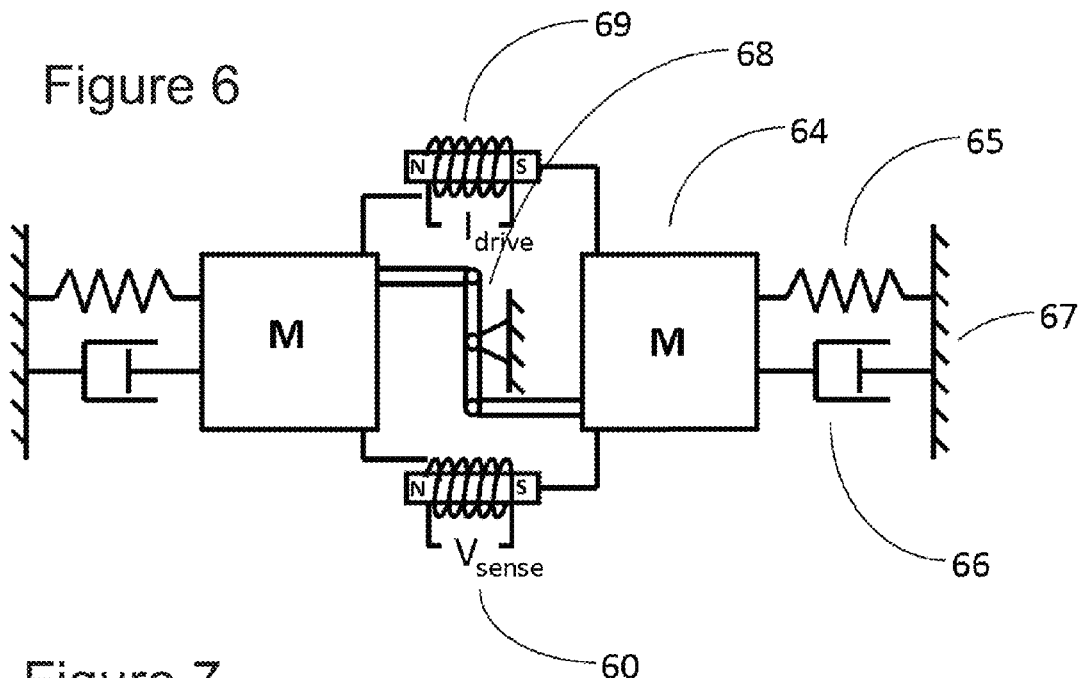
FIG. 6 is a model of the resonant sensor dynamic system.

A model of the resonant mechanical systems and the drive actuator and velocity feedback sensing system is shown in FIG. 6. Item 64 is one of the two motional masses. Item 65 is the spring element based upon the composite stiffness of the suspension legs. Item 66 represents the damping based upon all of the sources for dynamic motional losses, such as squeeze film damping, surface drag, and eddy current losses. Item 67 is ground, essentially the frame of the resonator. Item 68 represents the linkage that constrains the motion of the two masses to be 180 degrees out of phase and to be insensitive to cross axis shock, vibration and acceleration. Item 69 is the electromagnetic drive actuator ("drive electronics"). Item 70 is the velocity pickoff.

FIG. 6 depicts a model of the resonant mechanical systems and the drive actuator and velocity feedback sensing system. Two motional masses 64 are suspended within a fixed reference, or frame 67 by spring elements 65 which define the composite stiffness of "suspension legs." Damping components 66 (shown schematically) represent the damping based upon all of the sources for dynamic motional losses, such as squeeze film damping, surface drag, and eddy current losses. A linkage 68 constrains the motion of the two masses 64 to be 180° out of phase, and to be insensitive to cross axis shock, vibration and acceleration. An electromagnetic drive actuator 19 excites the system, and a velocity pickoff 70 records the velocity changes.

Linkage:

A dynamically balanced structure with opposing linear motion with a shared elastic foundation will typically result in the two halves resonating 180 degrees out of phase from one another. If the mass and/or stiffness imbalance is imperfect, these resonances can get out of phase. Also if the sensor is exposed to linear acceleration, shock or vibration this can disturb the resonance and potentially couple energy into the resonance. Therefore, to avoid these undesirable effects, it is preferable to add a linkage to force the two halves of the resonator to move 180 degrees out of phase. A linkage (such as shown at 68 in FIG. 6) constraining the two motional masses of the sensor may be included to constrain the opposing resonant element to move 180 degrees out of phase with each other. It substantially constrains both masses from moving side-to-side together. As shown as item 55 of FIG. 4 diamond shaped linkage with flexible beams on top and bottom may be utilized to constrain the two motional masses of the sensor to move 180 degrees out of phase with each other and substantially constraining both masses from moving side-to-side together. This ensures phase matching for dynamic balance and greatly reduces sensitivity to static g loading, shock and vibration.

In a preferred embodiment of the invention, a high aspect ratio diamond shape is employed to maximize motional mass movement while minimizing deflection at the tip. The elongated diamond shape allows the motion of the two motional masses to be large while the motion of the other corners to be minimized.

The motional mass sensor system may also include one or more sets of "V" shaped linkages with the end of each "V" connected to each of two motional masses and the center of the "V" connected to a linkage that provides compliance to motion perpendicular to the driven motion of the motional masses while rigidly constraining motion parallel to the driven motion of the motional masses constraining the two motional masses of the sensor to move 180 degrees out of phase with each other and substantially constraining both masses from moving side-to-side together.

The motional mass sensor system may alternatively include one or more rocker linkages with opposite ends of the rocker arm connected to each of two motional masses and the center of the rocker arm connected the frame thereby constraining the two motional masses of the sensor to move 180 degrees out of phase with each other and substantially constraining both masses from moving side-to-side together.

Motional Mass Design:

The design of the motional mass has a large impact on the detection signal frequency change relative to the resonant frequency. It is preferred to keep the active detection surface area large relative to the total motional mass in order to optimize the signal-to noise-ratio.

Figure 7:
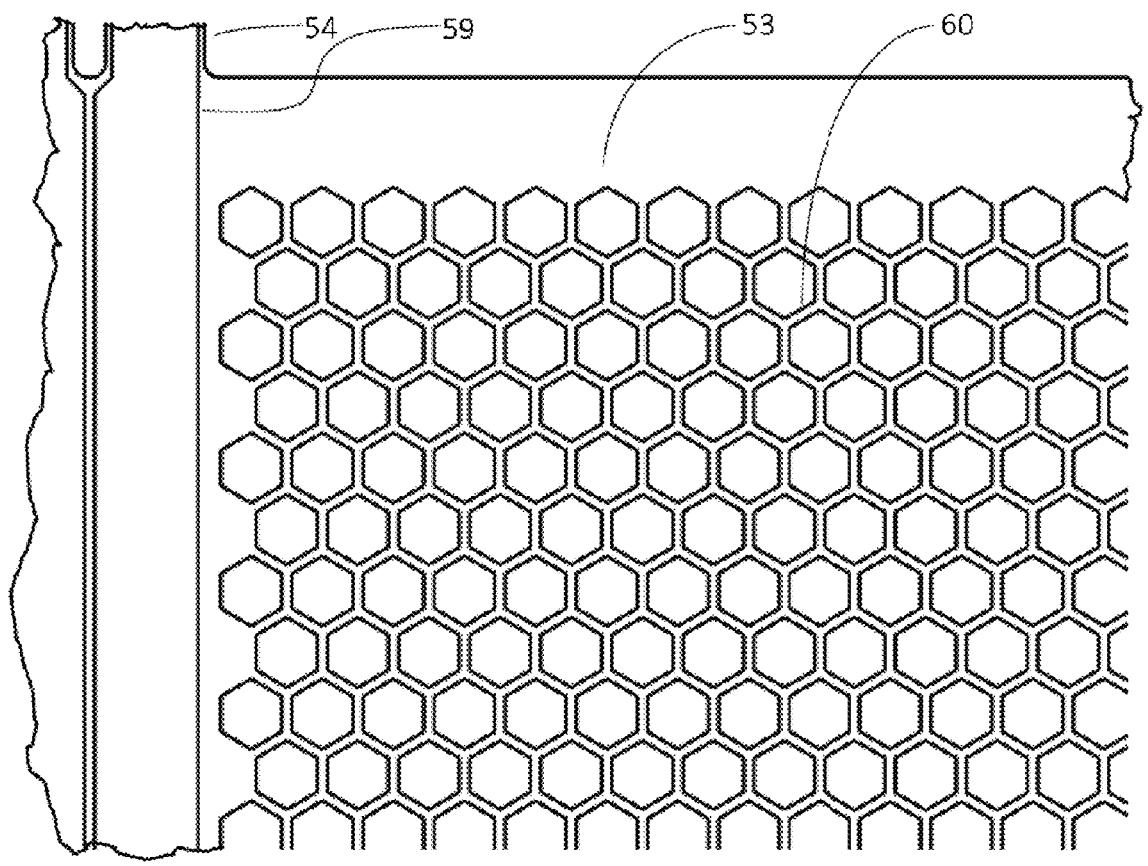
FIG. 7 is a cutaway illustration of a portion of the hexagonal hole sensor grid.

A preferred embodiment has a honeycomb structure as shown as item 53 in FIGS. 5 and 7 which provides for rigidity, low mass, the highest surface area to weight ratio for a flow thru sample measurement. The through-hole honeycomb, shown as item 60 in FIG. 7, design forces airflow through channels for maximum collection efficiency. The holes are desirably large relative to the sample geometry yet small relative to the air circulation dynamics, on the order of 30 microns, and can be of unique shapes as to maximize performance known to those skilled in the art such as cylindrical, hexagonal, and 60 degree lattice grid. The air flow is blocked and the fan is turned off during precision measurement. A key design objective is to minimize the weight of the resonant structure and to maximize the captured mass to maximize the period T change, $\Delta T/T_0$ for maximum sensitivity. The key trade here involves the use of hexagonal holes, round holes, or something in between. Round holes are best for coating uniformity whether by vacuum deposition, sputtering or liquid application. Hexagonal holes provide the best stiffness to weight ratio. It is advisable to add small radius in the corners to reduce stress concentration in the brittle silicon material of the hexagonal shape. MEMS processing will generate either shape accurately and baseline is round holes.

One embodiment uses a thin flat plate with no holes to serve as the sensing element. This plate is then coated with the chemically sensitive element to facilitate chemical or biological detection. Another embodiment of this uses nano-structures to increase surface-to-volume ratio on a flat plate. For example, carbon nano-tubes can be connected to the plate and the biochemically detective coatings can be attached to the carbon nano-tubes. Or silicon nano-wires can be generated on the surface to increase the surface-to-volume ratio. Porous silicon can also be etched on the motional mass to create a high surface area to mass ratio.

Figure 8:
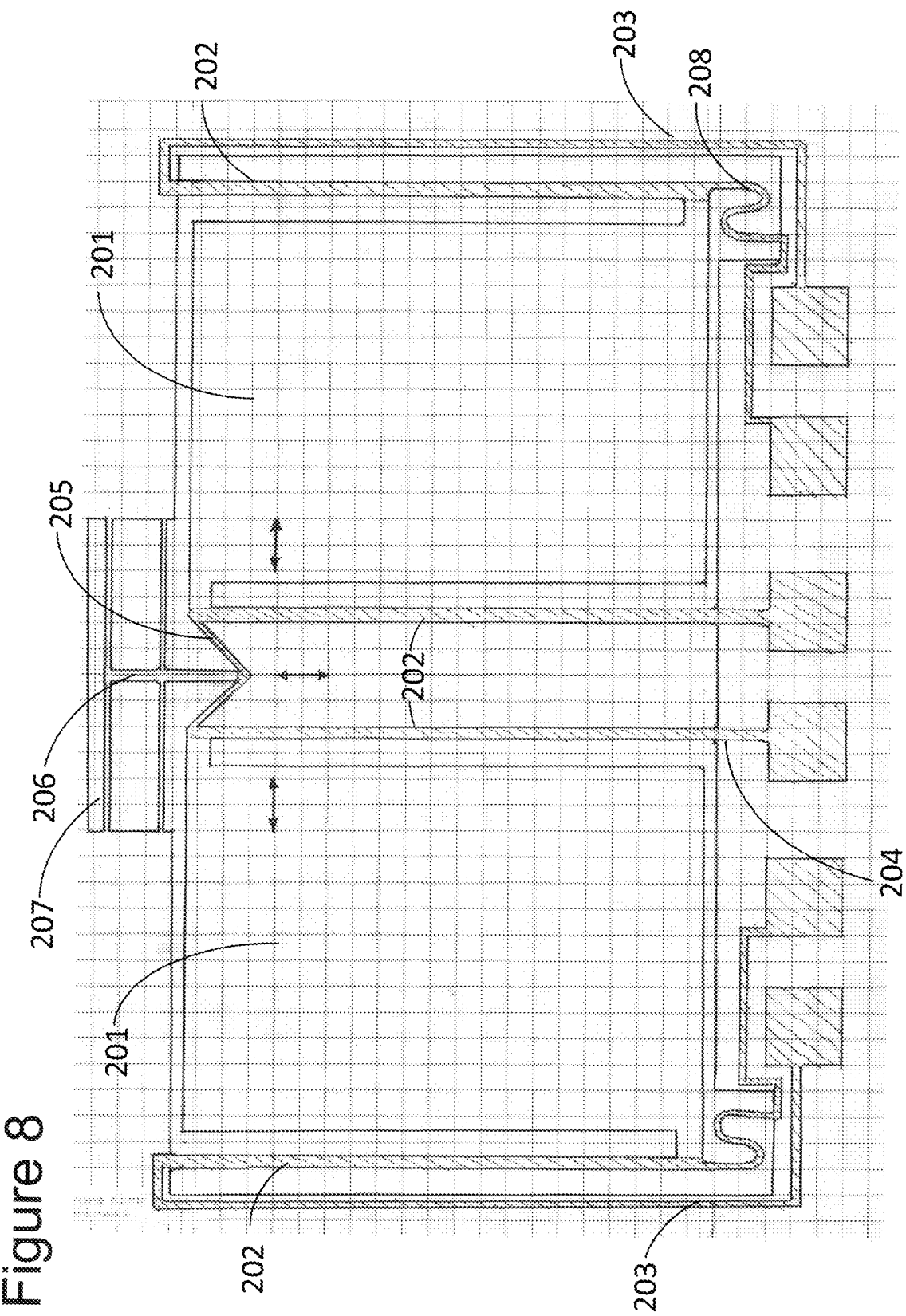
FIG. 8 is a sectional view of a sensor mechanization with a "V" link for connecting the two halves.

FIG. 8 depicts a sensor embodiment using two legs per half of the sensor. These legs, item 202, are separated to provide rotational stiffness while allowing compliance for rotation induced from foreshortening of the legs at large displacement resonant amplitudes. It also depicts a pair of drive electrode turns, item 203, and one sense electrode turn, item 204. It is possible to add more traces on the same leg if the leg is sufficiently wide and the resultant resistance increase is acceptable. This mechanism utilizes a novel "V" mechanism Item 205, to ensure that the two halves of the mechanism are precisely 180 degrees out of phase in their motion for dynamic balance. In this embodiment, when the two motional masses move toward one another, the folding up of the "V" drives rod, item 206, down in a linear motion due to the constraint of a pair of flexures shown as item 207. It also is stiff against lateral accelerations for vibration insensitivity. It also provides stiffness to control out of plane resonant modes. Item 201 of FIG. 8 is the motional mass. Item 208 is a very flexible structure used to bring the conductor trace from the moving motional mass to ground.

Another version of this sensor could have two "V" mechanisms, one on the top and one on the bottom to achieve symmetry and better restraint of undesired modes.

Figure 9:
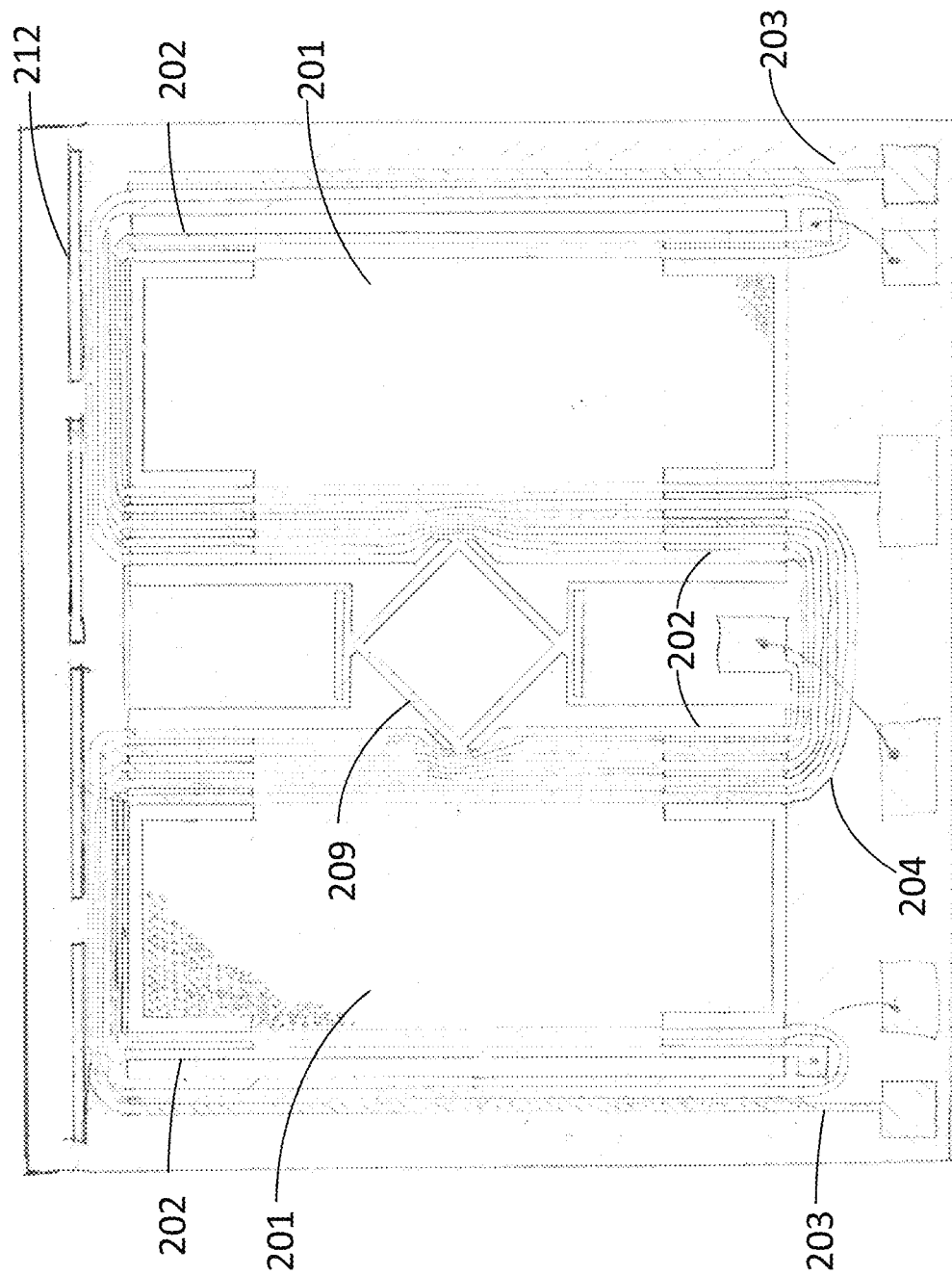
FIG. 9 is a sectional view of a sensor with double flexures with strain relief to attenuate foreshortening stresses.

FIG. 9 depicts a sensor design with multiple conductor turns on both the magnetic drive, item 203, and on the sense magnetic circuit, item 204. This is similar to a preferred embodiment in the use of a diamond connector linkage, item 209 except for the addition of a vertical mechanical strain relief, item 212, to relieve the axial tension resulting from foreshortening resulting as a result of large displacement of the resonant amplitude. Without strain relief, large displacement can add a third order stiffness term that causes the frequency of resonance to be more highly coupled to the deflection magnitude control loop stability. Mass balancing by either material subtraction (laser trimming) or addition (sputtering) can be used to trim the mass balance of the two paddles to precisely align the resonant frequency of each half of the sensor to reduce losses and coupling to the surrounding structure, thereby increasing resonator Q and minimizing interaction with surrounding structural resonances. Similarly, the stiffness term from the beams can be trimmed to minimize coupling and energy loss to surrounding structures.

Figure 10:
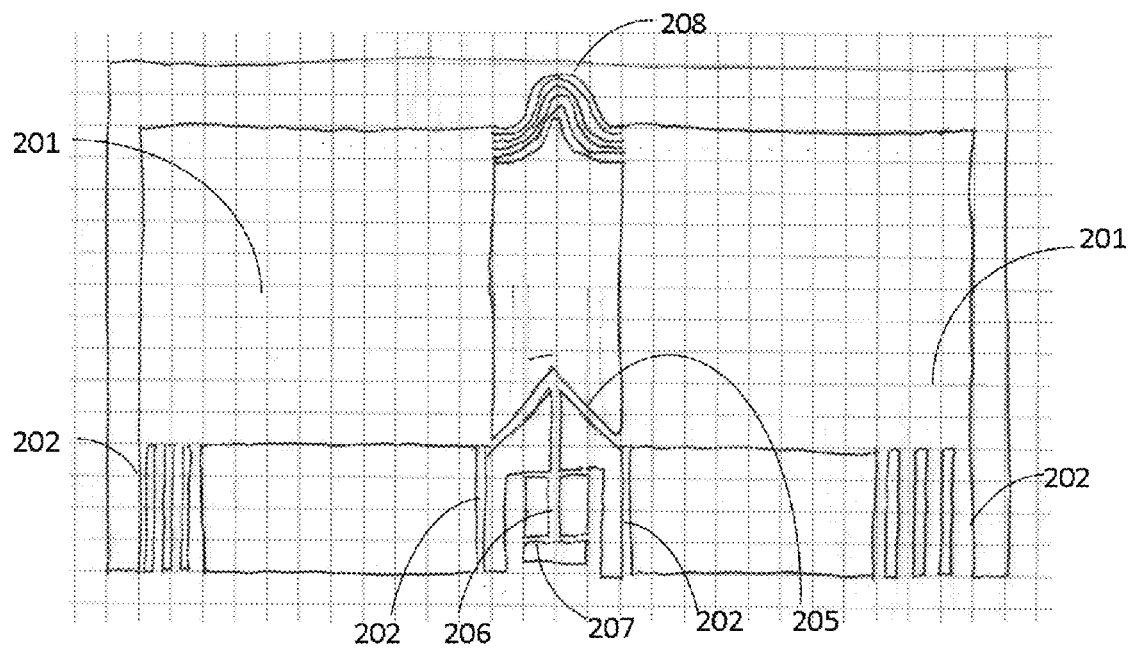
FIG. 10 is a sectional view of a single-sided suspension for strain relief.

FIG. 10 depicts a sensor that includes multiple turns of the sense and drive conductor traces. It is shown with a drive that employs one trace and the sense using the other three traces. The advantage of this design is the low mounting stress due to single sided design of the suspension, item 202. This design is non-optimal in several ways. The drive and sense circuits have a high level of mutual inductance. It also utilizes the "V" connection system 205. Furthermore, it utilizes fly wire conductors 208 between the two sections. The fly wires traverse between moving segments at the top to ensure maximum electromagnetic transduction efficiency.

Figure 11:
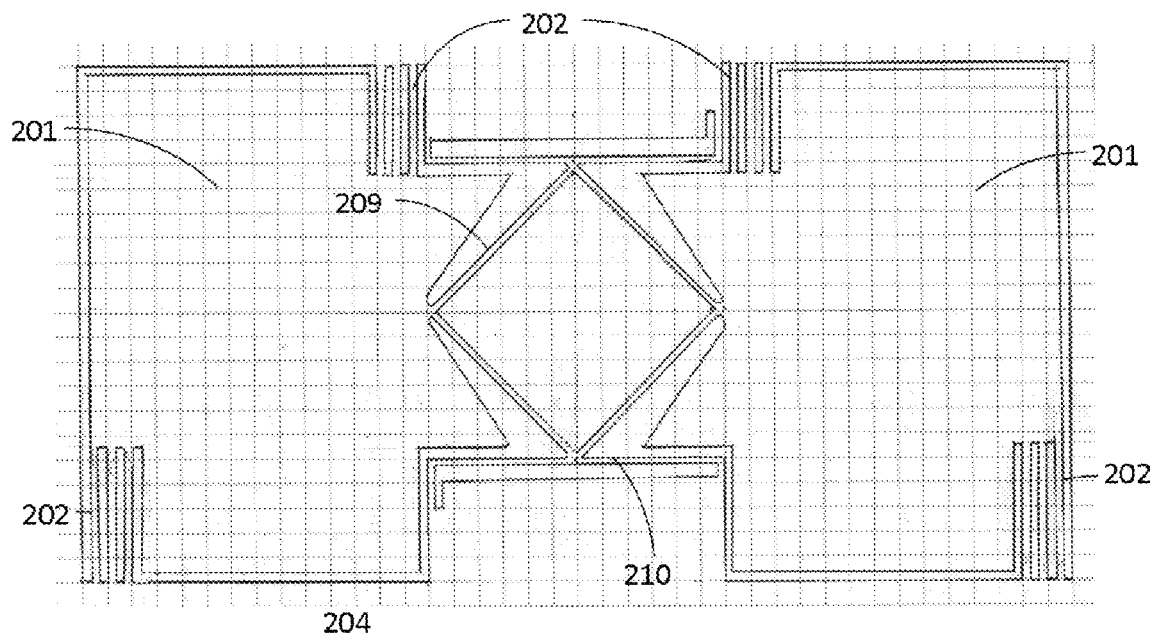
FIG. 11 is a sectional view of a sensor design with strain relief and diamond link.

FIG. 11 is a unique design with several design benefits. The suspension elements, item 202, allow modest strain relief by allowing the sensor halves to rotate to relieve stress. The dynamic reaction forces are precisely matched. They are connected by an advantageous diamond suspension item 209 connected to end flexures, item 210, which provide horizontal stiffness and vertical compliance. Which together control the motion of each half of the sensor, item 201, to be precisely 180 degrees out of phase. The conductive traces, not shown, run diagonally from the lower legs to the upper legs by essentially the shortest path to minimize resistance. Outside from the motional element of the sensor, the traces loop around to form a continuous magnetic drive and sense loops.

Figure 12:
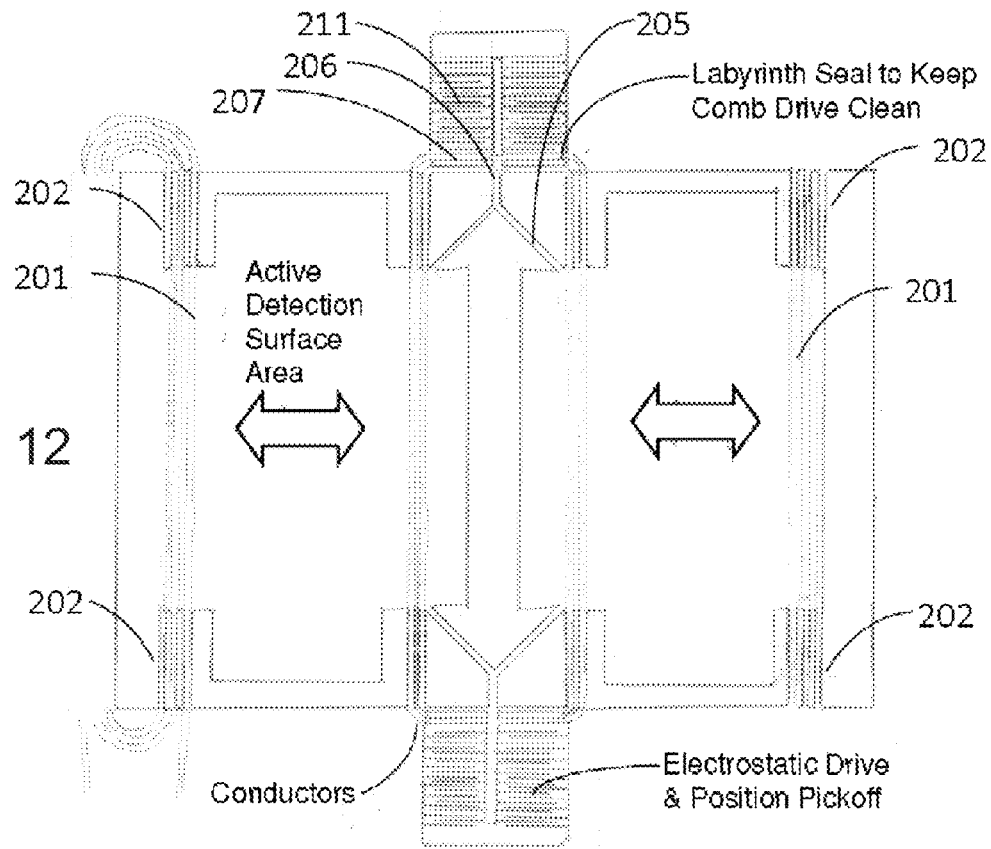
FIG. 12 is a sectional view of a sensor with electromagnetic drive and sense with labyrinth dust seal.

FIG. 12 depicts a sensor that utilizes electrostatic drive and capacitive position pickoff. Parallel capacitor plate sets 211 provide the physical structure for driving the motion and sensing the position. The position pickoff can share the same capacitor plates by measuring impedance of the plates with an alternating current far in excess of the resonant frequency of the mechanism. The motion is driven by applying a drive voltage synchronous with the driven resonant frequency. The flexures, item 207, hold the vertical alignment of the capacitor plates and the vertical structure, item 206. These flexures are rigid against horizontal motion. The "V" structure, item 205, converts the opposing horizontal motion of the two sensor halves into vertical motion of the capacitor plates and vice versa.

Figure 13:
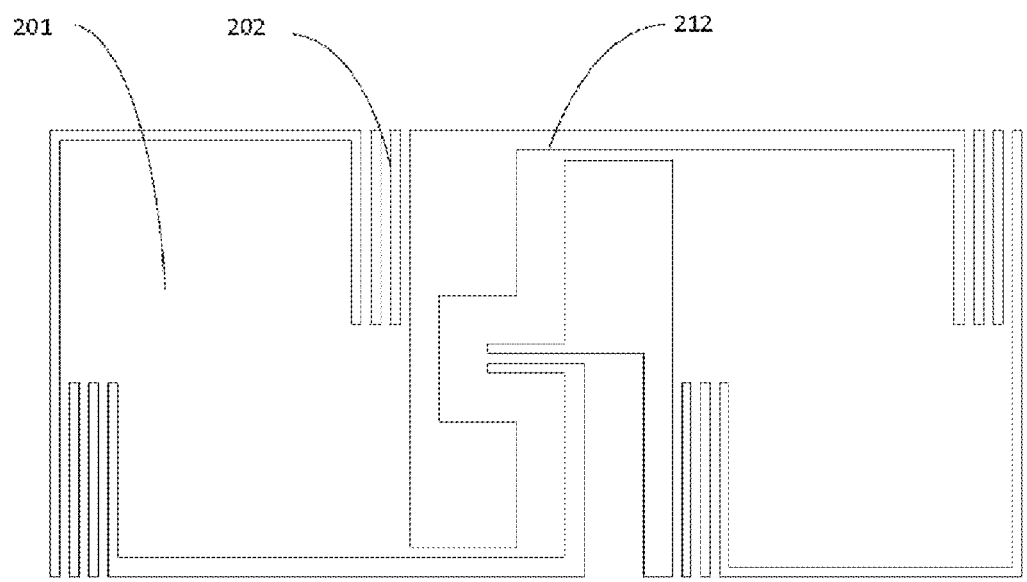
FIG. 13 is a sectional view of a sensor employing a rocker linkage to constrain the motion of the two halves of the sensor.

FIG. 13 depicts an exemplary device with excellent dynamic symmetry and excellent stiffness. The connective element utilizes a rocking connector to control motion. Excellent dynamic balance also requires that the motion of the two halves of the resonator is preferably precisely 180 degrees out of phase. In an extremely accurate device, this would occur naturally by the coupling through the ground mount. This approach degrades rapidly in the face of linear and angular acceleration and vibration. In a real world device, it is preferable to force the two halves of the sensor to move in precise opposition. This requires a mechanism capable of controlling this motion relative to the frame without imparting undesirable effects.

It should be noted that the sensor can be made to operate in wet and dry conditions. The Q will be degraded in wet operation. Cleaning the sensor with dry nitrogen and or helium will promote improved accuracy in wet conditions. This phenomenon can be mitigated by collecting the sample in the wet condition and drying the sensor prior to data collection. DC current can be passed through the coils to provide power for the heating. An alternative heating approach is to add a cover plate with micromachined conductors over the sensing area which are a gossamer, freely suspended, resistive heating element in close proximity to the sensing area. The sample media, gaseous or fluid, can pass freely through this structure. Also, the highest Q and hence accuracy can be achieved by testing in a near vacuum. This can be accomplished by adding vacuum-capable valves between the sensor intake and the sensor output. In one configuration, the vacuum pump can also serve as the output valve to reduce complexity. The collector grid could also be included in the vacuum-capable volume with the advantage of flashing the concentrated sample after evacuation to optimize sample collection efficiency and minimize moisture loading related errors.

Materials and Processing:

The choice of materials for the sensor has a major impact on performance. The desired material should have the following characteristics: high strength, high fatigue limit, excellent mechanical stability, low coefficient of thermal expansion, low modulus of elasticity temperature sensitivity, small grain size or single crystal, high temperature capability, and ease of fabrication.

A preferred embodiment utilizes single crystal silicon for the ultimate stability. Fused silica is also a viable material candidate, but is more challenging to generate thin vertical suspension legs. Other materials will also suffice, but typically without the stability, predictability and accuracy and high Q essential for low noise, allowing shorter sample times. Other materials also may lead to very low power to sustain the resonance, supporting battery operation.

Figure 14:
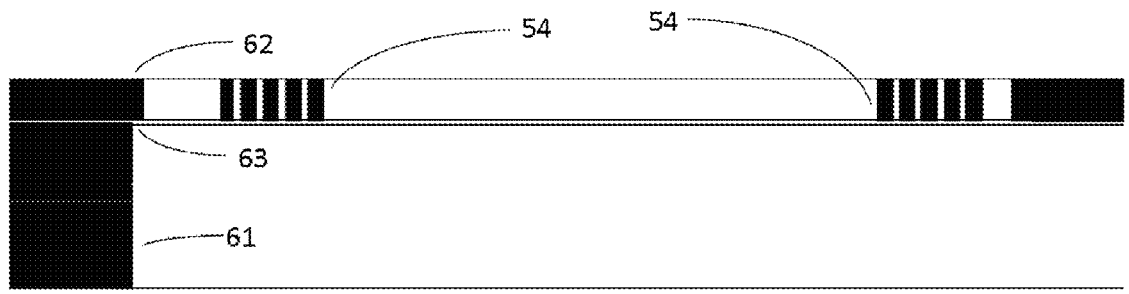
FIG. 14 is an illustration of the cross-section of the sensor suspension legs.

A preferred embodiment for the resonant element of this invention is single-crystal silicon with (low doping levels.) It is also uses silicon-on-insulator (SOI) as depicted as item FIG. 14 to isolate conductors and structures from one another. The terminology for SOI wafers is as follows. The top layer, typically thinner than the bottom layer, is called the active layer. The middle layer is the oxide layer, providing insulation between layers. The bottom layer is called the handle wafer. Item 12 of FIG. 14 is the frame structure in the active layer. Item 54 of FIG. 6 is a cross section of the motional mass suspension flexures. Item 61 of FIG. 6 is the handle wafer structure. Single-crystal silicon has a virtually infinite life at the design loads of this application. It has strengths well beyond high strength steel for survival in extremely rugged environments. Single-crystal silicon bulk micromachined devices are far more stable than surface micromachined devices. Deep reactive ion etching (DRIE) can be employed to generate highly accurate 2.5 dimensional geometry. This is ideal for out-of-plane beam fabrication as shown as item 54 in FIGS. 7 & 14.

An alternate material, crystalline quartz has advantages in the ability to employ the piezoelectric properties of quartz to both drive and sense the resonant frequency. By orienting the [1 1 1] crystalline planes with the vertical wall of the beams, the structure can fabricated using surface photolithography. With the use of metallic conductors on the surface and sidewalls oriented independently with sidewalls in positive and negative stress, the resonance can be driven by applying voltage to one or more beams and motion sensed by measuring charge output from one or more of the other beams. Crystalline quartz also has the advantage of very low internal damping losses leading to high Q resonance.

Resonator Forcer and Pick-Off Design:

It is necessary to drive the desired resonant mode at a constant amplitude. This requires a means of driving the resonance and a means to accurately detect the amplitude or velocity of motion. A closed-loop control system is then used to maintain resonant amplitude.

Magnetic Drive with Back EMF Velocity Sensing:

A preferred embodiment of the sensor system employs conductive traces across the moving element oriented substantially orthogonal to the driven resonant motion as shown in FIG. 3 item 84. The sensor is identified as item 51. The plenum which directs the flow of air directly over the collection grid is shown as item 83. The magnetic field is oriented substantially orthogonal to the conductive trace(s). This is depicted in FIG. 3. The vacuum chamber, item 79 also serves as the magnetic return path. Item 81 depicts the Neodymium Boron Iron permanent magnets, oriented with the north-south field in the same direction. The vector of resonant motion is orthogonal to the magnetic field and the axis of the conductor. In the case of the drive circuit, current flows through the conductive traces generating a Lorentz drive force to sustain resonant. In the case of the sense circuit, the motion of a conductor perpendicular to the magnetic field generates a voltage due to back electromotive force (EMF). Multiple turns of the conductive traces are used to increase force and sense signal magnitude.

Figure 15A:
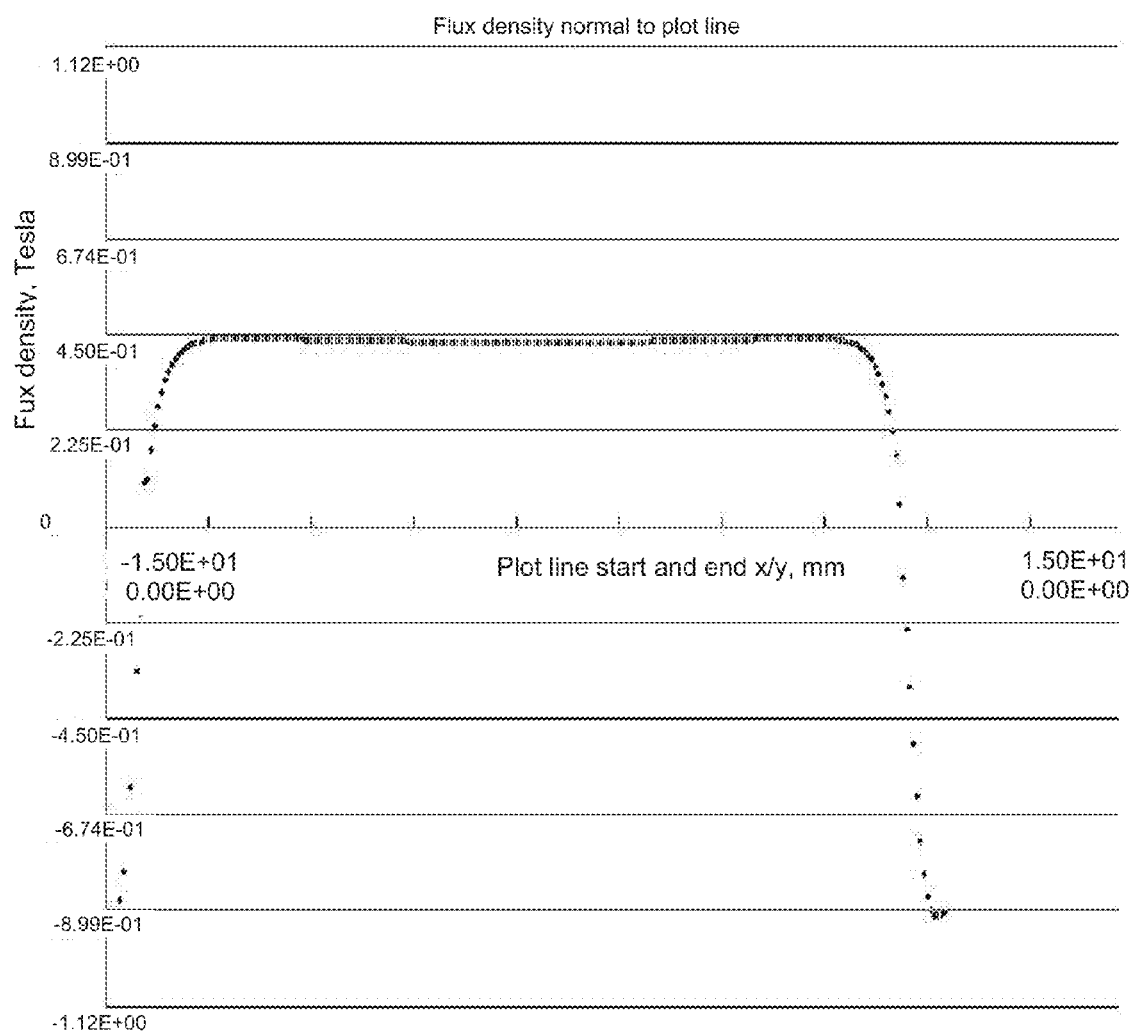
FIG. 15(a)-(b) are cutaway illustrations of the sensor in the magnetic field generated by permanent magnets which alternately change field direction
Figure 15B:
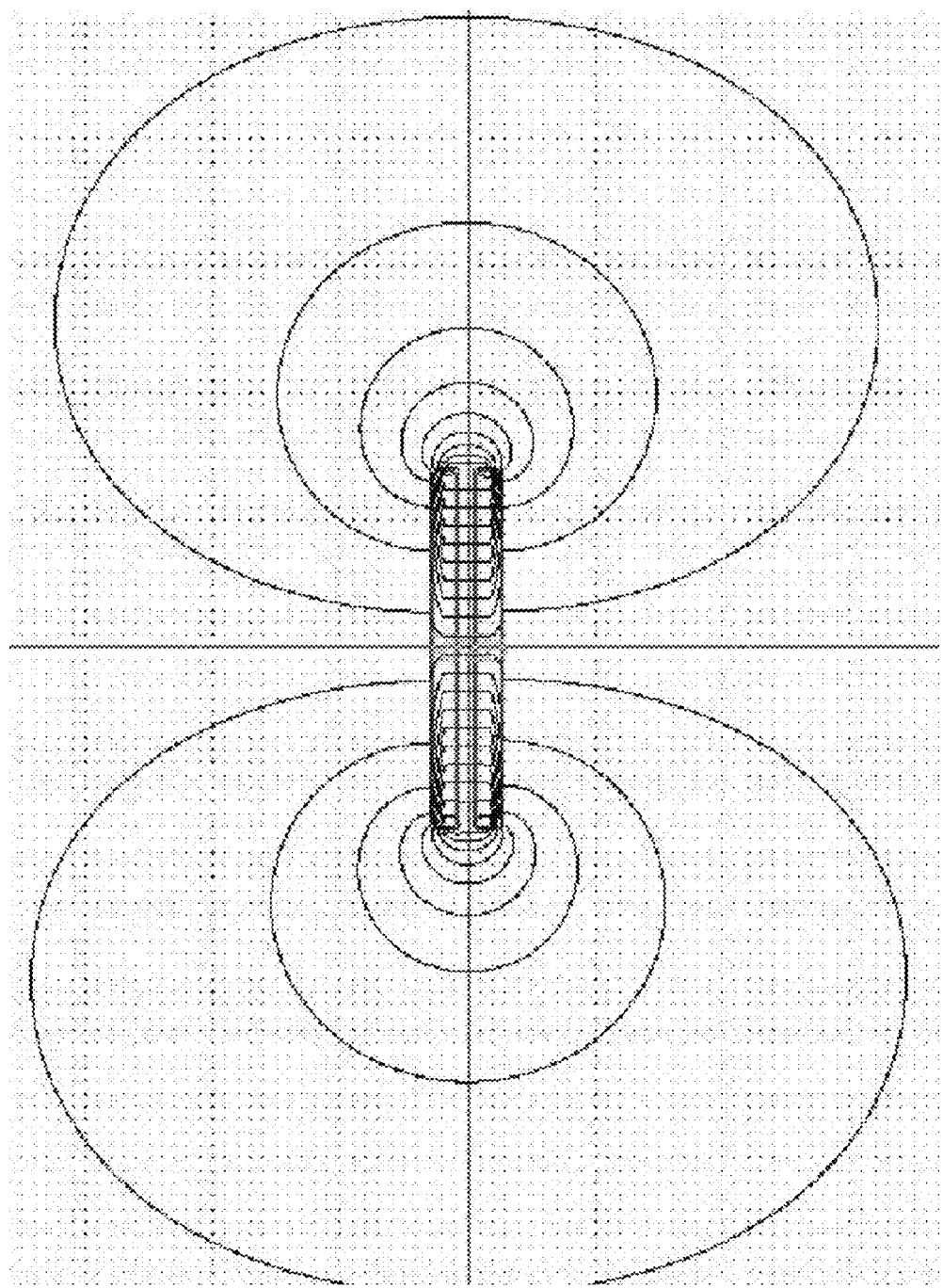
Figure 16:
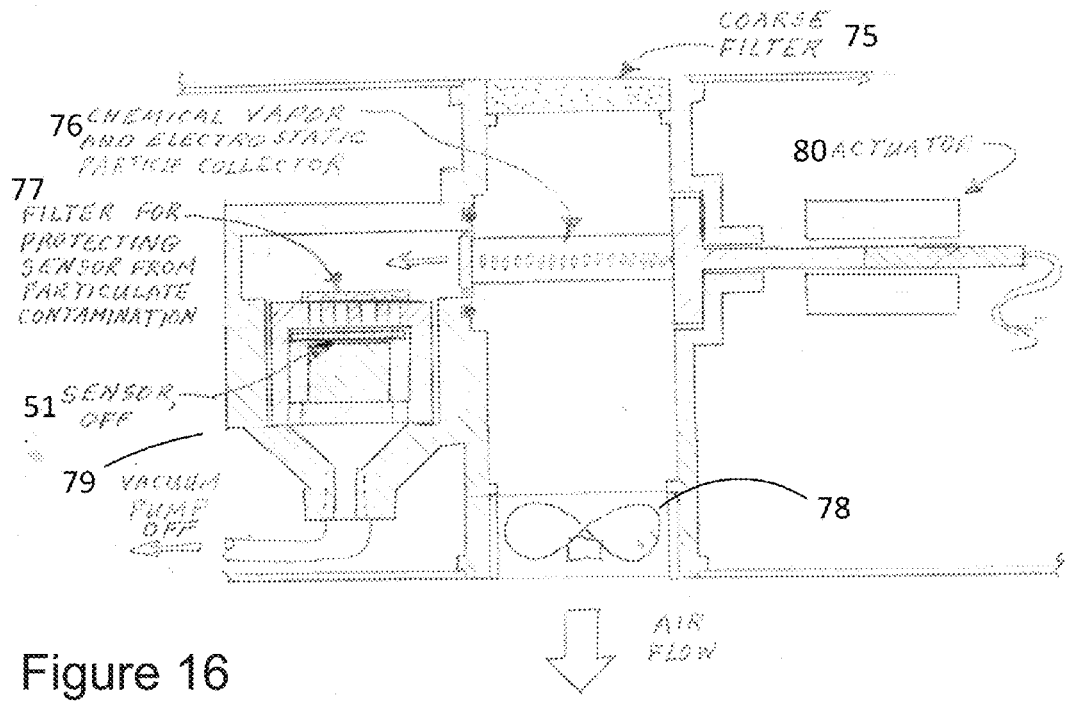
FIG. 16 is a partial sectional view of a sample collection/concentration system with two chamber design with collection grid shown in collection/concentration position.
Figure 17:
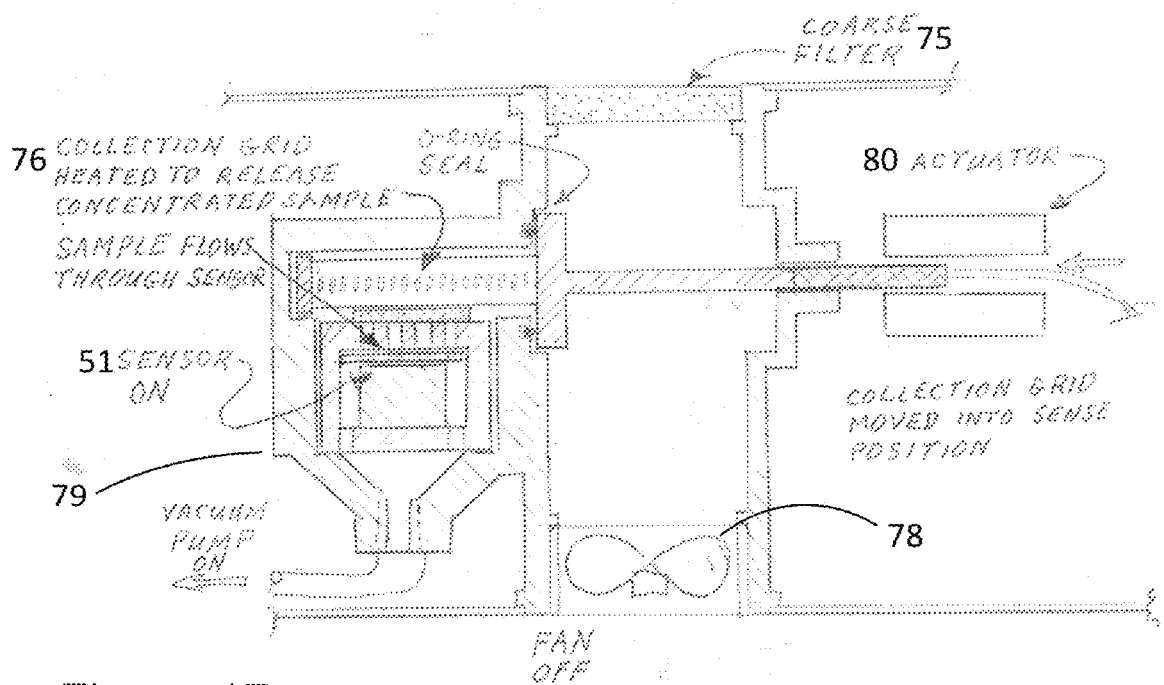
FIG. 17 is a partial sectional view of a sample collection/concentration system with two chamber design with collection grid shown in test/analysis position.
Figure 18:
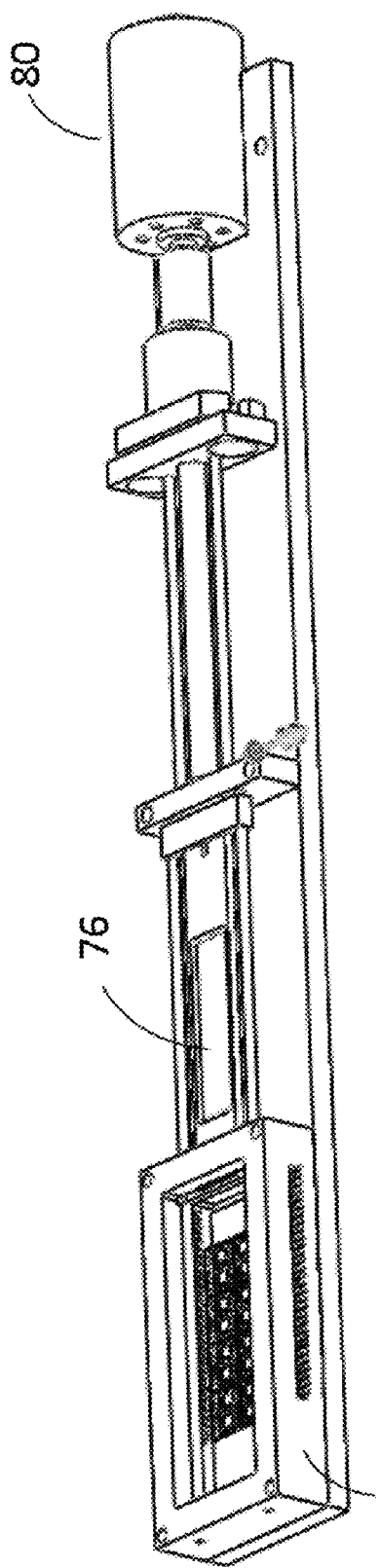
FIG. 18 is a perspective view of a two chamber mechanism design with collection grid shown in collection/concentration position.
Figure 19:
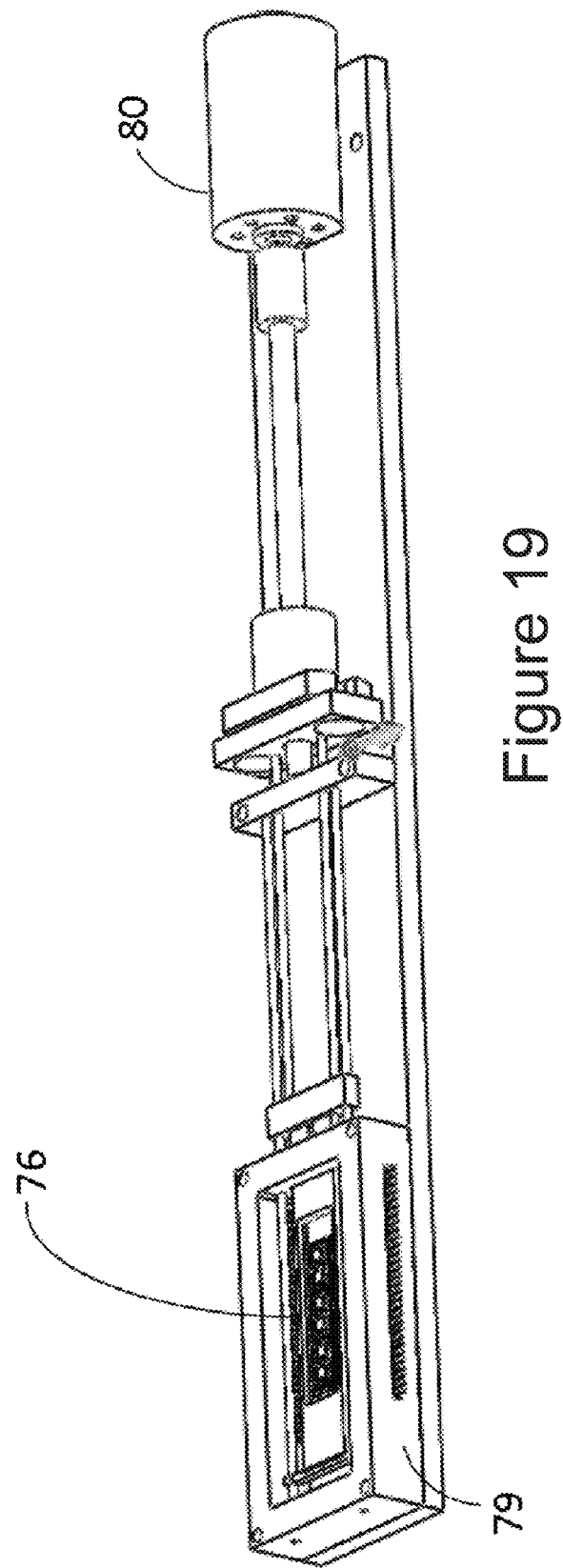
FIG. 19 is a perspective view of a two chamber mechanism design with collection grid shown in test/analysis position.

The magnetic field normal to the surface for the sensor is preferably generated by a set of permanent magnets with flux shaping back irons and side irons, items 82 of FIG. 3. This approach generates a high flux density across the sensor array as shown in the magnetic analysis plot of FIG. 15*a*. This magnetic field generator creates a very uniform field with the B field perpendicular to the motion of the sensor as shown in the magnetic analysis plot of FIG. 15b to minimize energy coupled into out of plane motion. The stability of the magnet over time and temperature is important in that a change in field strength changes the amplitude of resonance and can generate an undesirable frequency shift due to the amplitude-frequency sensitivity of the resonator. The early prototype of a permanent magnet and return path capable of generating a magnetic field strength in the sensor of approximately 6 K Gauss.

An alternative embodiment utilizes a set of magnets without a return path. This approach has a significant cost advantage. However, the resultant field strength is slightly lower. The field can be or circulated with the same field orientation across the entire sensor as depicted in FIG. 3 or locally recirculated with alternating field directions. Note that an alternative embodiment would employ magnet(s) only on the side of the sensor containing conductor traces.

A novel approach to solving this problem is to utilize an electrostatic drive and capacitive sense pickoffs. They could even share the same plates such as a comb drive with a high frequency voltage signal to detect capacitance and a relatively low frequency drive signal so as to avoid interaction. The comb drive is desirable because of its linear voltage-to-force response and its linear position-versus-capacitance response, making control system design straightforward. The extreme negative with electrostatic drives and capacitive pickoffs is the propensity to become contaminated and to jam. They also tend to have high motional losses due to squeeze film damping resulting in low Q at atmospheric pressure. The high field strength between the plates draws particles into the gap much like an electrostatic air cleaner.

Piezoelectric Drive and Sense:

Employing the alternate material of crystalline quartz has advantages in the ability to employ the piezoelectric properties of quartz to both drive and sense the resonant frequency. By orienting the [1 1 1] crystalline planes with the vertical wall of the beams, the structure can fabricated using surface photolithography. With the use of metallic conductors on the surface and sidewalls oriented independently with sidewalls in positive and negative stress, the resonance can be driven by applying voltage to one or more beams and motion sensed by measuring charge output from one or more of the other beams.

Alternative Embodiments

It is well known to those skilled in the arts that other methods are available to those skilled in the state of the art to drive and sense the resonator motion. Additionally, any combination of drive and sense technology can be used to create a control system for the resonance. This includes optical, inductive, piezoresistive sensing technology and inductive, photonic thermal and other drive methodology.

The most notable novel aspects of this sensor design include the following:

Virtually perfect dynamic balance of the resonant element to minimize reaction forces to the mounting structure for high Q, excellent stability, low mounting sensitivity, low coupling to structural resonances.

Novel coupling mechanisms to constrain the motion of each half of the resonator to be held precisely 180 degrees out of phase with matching amplitudes relative to the mounting structure to ensure dynamic balance and insensitivity to acceleration, shock and vibration MEMS processing for extreme accuracy, low cost, Utilization of in-plane resonant motion to maximize Q by minimizing squeeze film damping effects.

Separation of adjacent structure from the resonant structure to minimize shear damping and squeeze film damping.

Single crystal silicon construction for unparalleled mechanical stability. The resonant frequency is defined by the mass, stiffness, and geometry; all stable to parts-per-billion levels in single crystal silicon.

Novel honeycomb structure with high stiffness-to-weight ratio and with optimal surface area-to-volume ratio for maximum sensitivity to coating mass changes Conductor traces on the resonator in conjunction with a magnetic field mutually orthogonal to the conductor trace and the linear motion vector provides for high authority drive of the resonant motion by running current through these conductors in the proper phase with the resonant motion.

Utilization of more than one conductor across the resonator to increase force derived from a given drive current flow.

Conductor traces on the resonator in conjunction with a magnetic field mutually orthogonal to the conductor trace and the linear motion vector provides for velocity sensing in the form of a large amplitude voltage signal as a linear function of the resonator velocity with low resistance for low Johnson noise. Utilization of more than one conductor across the resonator to increase voltage signal for a given resonator velocity.

The use of a high impedance resonator velocity pickoff circuit to eliminate current flow in the conductors thereby reducing velocity pickoff noise due to shot noise.

Utilization of physically separate drive and sense conductor loops on a given resonator to minimize mutual inductance and the resultant coupling of drive current shot noise into the velocity pickoff circuit.

Use of an electromagnetic drive and sense control loop to provide accurate control of the resonator amplitude to minimize the effects of amplitude-frequency coupling on the accuracy of measurement.

Introduction of compliance in the suspension system of the resonator to minimize foreshortening stresses and the resultant amplitude-frequency sensitivity.

Suspension system design ensuring precise linear motion of the center of gravity of each half of the sensor for dynamic cancellation of forces and exact and opposite angular acceleration of each half of the sensor for cancellation of torques.

Ability to use direct current flow through the drive and sense conductor traces to heat the sensor.

Ability to measure the resistance of the drive and sense conductors to measure sensor temperature.

Ability to use the reference sensor as a temperature sensor through well defined temperature coefficient effecting stiffness of Si and hence resonator frequency.

Ability to use the drive and sense conductor traces to provide closed loop temperature control of the resonator.

Ability to use direct current flow thru the drive and sense conductor traces to heat the sensor for reset of biological capture coatings by releasing captured biological agents.

Ability to use direct current flow thru the drive and sense conductor traces to heat the sensor above the dew point to negate moisture mass loading of the resonator.

Ability to use direct current flow thru the drive and sense conductor traces to heat the sensor to rapidly dry the sensor after aqueous sample processing in preparation for a dry sensor measurement.

Ability to use direct current flow thru backside metallization to heat the sensor to rapidly dry the sensor after aqueous sample processing in preparation for a dry sensor measurement, to thermally reset the coatings, or to keep the sensing surface well above the dew point.

The process of applying backside metallization using vacuum deposition with the metal applied orthogonal to the plane of the wafer and the straight walls of the DRIE providing self masking.

The use of multiple thin, flat beams keeps the desired in-plane resonant mode frequency low while keeping the undesirable out of plane mode frequencies high for ruggedness and vibration insensitivity.

Sensor Array Design:

It is advantageous to fabricate the sensors into arrays. A preferred embodiment incorporates a plurality of sensors fabricated from a single crystal of silicon at the wafer level. This is cost effective for sensor fabrication and sensor system assembly. The use of a monolithic structure of single crystal silicon has the advantage of ultimate mechanical stability and low internal mechanical losses in resonance to maximize Q.

The sensors are grouped into an array wherein a plurality of sensors can be diced from the wafer into a single array for ease of wire bonding assembly and testing.

Embodiments employing multitudes of sensors in a single array are conceived for performing chemical analysis based upon correlation of the array with a known response to the target chemical.

In a preferred embodiment, eight resonators are slightly offset in frequency to allow simultaneous operation with greatly reduced potential for cross coupling. High Q mechanical resonators have a high potential for cross coupling mechanically, electromagnetically, and electrically, generating undesirable noise. In the worst case, if frequencies of two high Q resonators get very close, they can lock onto each other.

A preferred embodiment of the resonant chemical sensor system includes multiple resonators each with different chemically active coatings to provide chemical detection and compound identification based upon the signature of frequency changes for the different coating types. It also includes resonators with inactive coatings or no coatings at all to serve as a reference resonator. This frequency is used to reject common mode errors such as resonator frequency temperature sensitivity and clock inaccuracies. A sensor for humidity, temperature and pressure is desirably included to compensate for each sensor's sensitivity to these parameters.

In a preferred embodiment of a sensor array with multiple resonators, the frequency of each resonators is separated so that they will never cross in frequency. They are also separated for enough in frequency to virtually eliminate cross-talk when operated simultaneously. Furthermore, the sensors with the closest resonant frequencies are separated spatially to minimize electromagnetic and mechanical cross coupling.

The fundamental architecture of the sensing system involves the comparison of the resonant frequency of one or more inactive reference resonators to the resonators with active coatings. Two types of reference resonators are desired. One has no coatings and provides a baseline reference of ceramic and metal elements that do not absorb moisture. The second reference resonator is identical to the active resonator(s) except it is non-agent sensitive e.g. non-biologically or non-chemically-reactive. This reference resonator experiences moisture absorption equivalent to the active resonators. Together, the reference resonators provide insensitivity to common mode errors such as contamination, aging, moisture absorption, and temperature sensitivity. Clock stability requirements are also reduced by orders of magnitude. They can also provide a measurement of moisture in the sensors for use in the calibration algorithms.

Multiple chemical compounds can be used in the sensor array to aid in discrimination for reduced false positive errors. The present resonator array embodiment has six sensing elements. A preferred embodiment will likely have on the order of 8 to 12 sensing elements to provide for use of more than one sensor with identical active coatings can also be used to "vote" on the presence of a threat chemical response. It may also be optimal in some cases to detect the "contaminant" chemicals capable of producing false positive indications to reduce false positive probability.

The sensor array shown in FIG. 1 contains multiple resonators physically separated by a common structure to minimize sensor size and assembly cost. They could also be separate sensors arranged into a sensor array. The resonators should be separated in frequency to avoid cross-coupling between channels or frequency cross-over during sensing life. In effect, this creates a chemical nose with the use of multiple sensor coating technologies.

Sensor Manufacturing:

A preferred embodiment utilizes single-crystal silicon MEMS processing. It is also possible to use other materials and processes to crate this device. Surface micromachining in polysilicon is possible. Electroplating of MEMS scale devices is also possible using processes such as LIGA. Crystalline quartz could also be utilized with chemical micromachining and use of piezoelectric properties for derive and sense.

Single-crystal silicon MEMS processing with low doping levels was selected for the following reasons:

Low cost wafer level fabrication and assembly

Extremely high accuracy, <0.1 µm, 3 sigma dimensional accuracy

Virtually infinite life is intrinsic to single crystal silicon resonators

High strength and small size provides for survival in extremely rugged environments Proven process sequence is relatively simple, requiring only two mask sets.

Single-crystal silicon bulk micromachined devices are far more stable than surface micromachined devices.

A preferred silicon wafer design is silicon-on-insulator. The thin top layer, shown as item 62 and 54 in FIG. 14, is the active layer. It is physically separated from the handle wafer, shown as item 61 in FIG. 14, by a buried oxide layer, shown as item 63.

One process sequence is as follows:
1. Procure six inch silicon-on-insulator wafers with top layer thickness of 50 microns and buried oxide layer thickness of 1.25 to 2.0 microns
2. Deposit "low stress" silicon nitride layer 2000 angstroms thick
3. Apply chrome layer with a thickness of 450+/−50 angstroms and a gold layer of thickness 5500+/−300 angstroms with a purity of 9999%.
4. Au resistivity shall be <=3.75 u ohm cm.
5. Spin photoresist, expose and develop photoresist pattern
6. Etch or lift off metallization pattern.
7. Spin thick photoresist, expose and develop photoresist front-side pattern for DRIE definition
8. DRIE holes and slots down to the buried oxide layer
9. Strip resist and clean wafer 10. Spin thick photoresist, expose and develop photoresist back-side pattern for DRIE definition
11. DRIE Backside opening down to the buried oxide layer
12. Etch buried oxide layer using 49% HF etch to free the paddle & flexure structures.
11. Strip resist and clean wafer
12. Probe wafer to measure continuity of traces, select viable die.
13. Provide protection for the devices in preparation for dicing
14. Dice the wafer
15. Clean parts; remove dicing protection and final clean parts
16. Wire-bond jumper connections on sensors with proper continuity and freedom of motion
17. Place parts in protective packaging to ensure cleanliness
18. FIB cross sections to evaluate footings on one resonator and SEM 4 sample resonators Sensor Coating Application, Measurement and Resetting:

The chemical sensor relies on the use of coatings of a material that changes mass when exposed to the target chemical. This change in mass is the driver for frequency change, the primary detection signal.

The chemical sensing system desirably includes a collection/concentration grid coated with a compound having high specificity affinity for the target chemicals placed in a high volume air flow condition to concentrate chemical vapors for subsequent release in a separate test/analysis chamber containing a chemical a sensor using heat to release chemical vapors from the coating on the collection/concentration grid. Furthermore, the chemical sensing system may incorporate a system to charge particles in the high volume air flow and use electrostatic forces to bind the particles to the collection grid for subsequent release of the absorbed chemical vapors in a separate chamber containing a chemical a sensor using heat to release chemical vapors from the particles on the collection/concentration grid.

The separation of the test/analysis chamber from the collection/concentration chamber provides an important particulate contamination function. Only the electrostatically bound particles enter the test/analysis chamber. This minimizes the potential for a particle to generate a false reading by attaching to the motional mass of a sensor. The collection grid also has coatings with high specificity for capturing the target chemical(s) and allowing the other chemical vapors to flow away with the main airflow. This greatly reduces the amount of non-specific binding of undesirable chemicals to the sensors which are not exposed to the airflow. The separation of the test/analysis chamber from the collection/concentration chamber allows the test/analysis chamber to be sealed and evacuated easily to increase resonator Q.

In accordance with one embodiment, a resonant chemical sensor system utilizing one or more resonators with chemically active coatings and one substantially identical sensor without chemically active coatings to serve as a reference resonator wherein the chemical detection signal is primarily the difference between the active resonator frequency or period shift and the reference resonator frequency or period shift.

In chemical sensing and biological compound sensing embodiments, an inactive insulating layer is applied over the sensors prior to active coating application. Many of the metals, chemical compounds, and biological coatings can be applied by bulk processes at the wafer level for minimum cost. Coatings can be applied to the active region of the sensor by many techniques. Thin film metallic coating can be applied by sputtering, chemical vapor deposition, electroplating, and physical vapor deposition, with the purely linear processes such as vacuum deposition, the wafer could require angular manipulation during deposition to cover all walls of the through holes. Chemical coatings can be applied by dipping, spraying, chemical vapor deposition, ink jet, wafer spinning, vapor, etc.

The biological coatings tend to differ in their application. Many cannot tolerate the extreme application environments such as temperature required by the detection process. As stated above, techniques such as liquid immersion, local spray, ink jet, and physical application are preferable. This thermal exposure can be a problem if the coating is damaged in the process, it is an opportunity if the coating is reset by the thermal exposure, assuming the coating is not damaged, the chemical attachment to the previously acquired pathogen can be broken, rendering the surface ready for reuse.

Metallization can be applied to the backside of the sensor for use as a resistive heater with very uniform current distribution. Heating of the sensor element is valuable for a number of reasons; the sensor can be dried rapidly after aqueous sample processing in preparation for a dry sensor measurement, heat can be used to thermally reset the coatings, heating of the sensing element can prevent moisture collection in humid environments by keeping the sensing surface well above the dew point, and the heaters can be used in conjunction with a temperature sensor to control the temperature of the sensor for improved measurement accuracy. This film can be applied using shadow masking and vacuum deposition. Vacuum deposition has the desirable characteristic of applying metal in a perfectly straight line. This allows the use of a self masking technique for low cost. This process of applying backside metallization using vacuum deposition with the metal applied orthogonal to the plane of the wafer and the straight walls of the DRIE providing self masking is effective due to the minute scalloping in the DRIE sidewalls that effectively breaks up continuity down the sidewalls.

New nanofabrication techniques are evolving rapidly. These processes, when mature, show great promise for use as biological and chemical sensor coatings. For example, carbon nanotubes provide extremely high surface area-to-volume ratios with attractive sample capture capabilities.

Sample Collection, Concentration and Processing:

Sample Collection:

FIGS. 16 and 18 are depictions of the sample collection system in sample collection mode. The coarse filter, item 25, removes large particles. The particles and vapors are collected on the grid defined as item 76. The fan, item 78, moves high velocity sample air over the collection grid.

When a sample is collected on the grid, the actuation system, item 80, moves the sample into the vacuum chamber, item 79, for analysis. At this point the vapors are absorbed into the coatings on the collection grid and the particles are firmly attached to the grid by electrostatic forces. This is a key unique feature which keeps dust out of the vacuum chamber. If particles were to enter the chamber, a secondary filter, item 77, is added to prevent dust from reaching the chemical sensor, item 51.

FIGS. 17 and 19 depict the chamber in the test/analysis mode. In a preferred embodiment, the process flow includes a pump down of the chamber to a low pressure with the collection grid enclosed. Subsequently, the collection grid is heated to a temperature just high enough to release the desired chemical constituents. The chemical vapors are then slowly drawn thru the sensor motional mass grids to selectively capture the desired chemical compound.

Sensing:

The resonant frequencies of the sensors in the grid are measured accurately after the remnant chemical traces have been evaporated from the previous test sequence. This serves as the reference frequency for determining the frequency change resulting from exposure to the collected chemical sample. In a preferred embodiment, the pre- and post-chemical exposure tests are run at an equal low pressure to maximize Q and to remove pressure imparted errors.

The motional mass sensor system may utilize heating of the motional masses to slowly raise the temperature of the chemical sensing element containing the concentrated sample while resonating at its resonant frequency to detect evaporating chemical mass based upon its vapor pressure as a function of temperature.

Electronics Design:

The electronics perform numerous functions in this biochemical sensing system. Their primary function is to establish the resonant amplitude at a precise displacement and at the natural frequency of the resonator. The sensor output is a low noise signal representing this resonant frequency of amplitude proportional to sensor frequency and oscillation amplitude. They also provide signal amplification, filtering, control thermal loops, perform signal processing for other sensors in the system, perform analog and digital signal processing, provide communication, run graphical user interfaces, operate sample collection, concentration and processing systems, provide high accuracy time, and provide GPS position (in special cases).

Two major types of resonator control loop electronics embodiments, analog and digital are described for this sensor system. The preferred embodiment of the sensor has two coils-one a drive coil for exciting the resonant sensor and the other a sense coil that detects the back EMF of the sensor. When the sensor is functioning in the expected mode, then the back EMF is a near sine wave operating at the frequency of interest and of amplitude proportional to the frequency and displacement amplitude.

Figure 20:
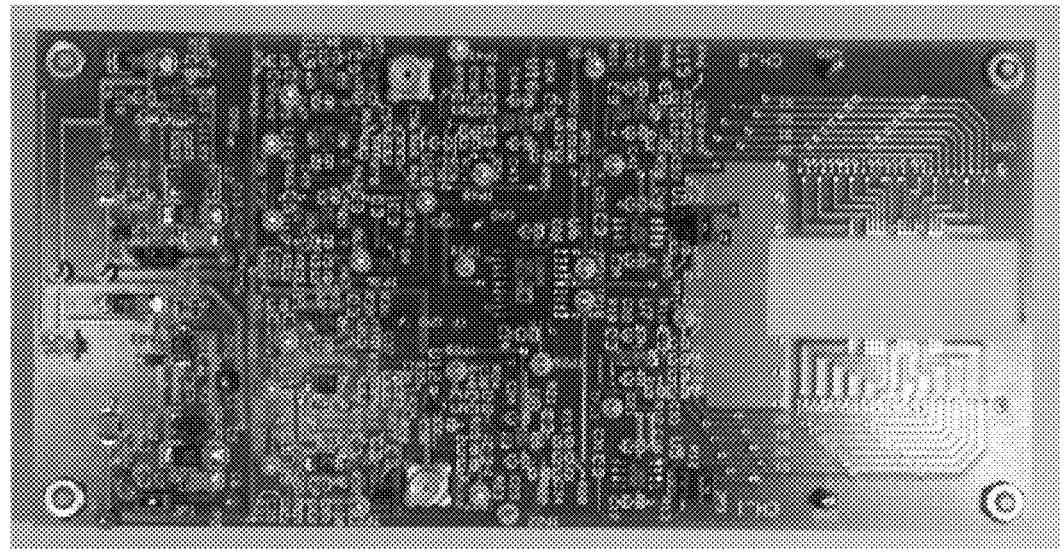
FIG. 20 is a plan view of an analog control circuit board.

Analog Signal Processing:

Analog signal processing has proven to be very effective and low noise in this application. Prototype analog electronics for driving an early prototype of this biochemical sensor are shown in FIG. 20. In this embodiment there are two tracking circuits as well as switching power supplies on the board. The inputs are the two sensors and the outputs are a precision square waveform of frequency equal to the resonant sensors.

Figure 21:
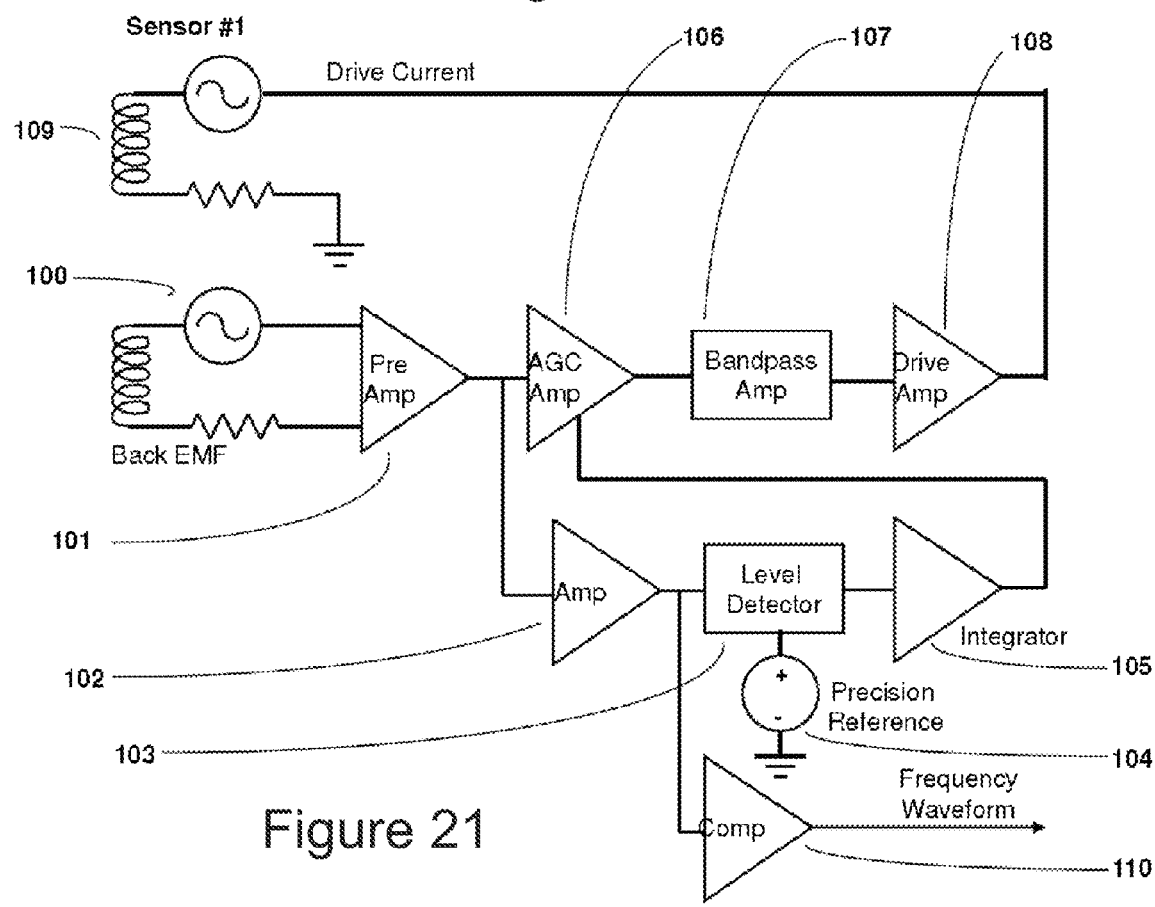
FIG. 21 is a block diagram of a single resonator analog control system.

The block Diagram for the analog electronics embodiment is shown in FIG. 21. The sense BEMF from the sensor, 100, is amplified by a low noise amplifier, 101, with noise characteristics of the order of 1 nv/sqrt (Hz) and its level shifted and amplified, 102, and its value is compared in a level detector, 103 with a precision reference, 104. The error signal is integrated, 105, and controls the gain of an automatic gain control (AGC) amplifier, 106. This signal is processed through a Bandpass amplifier which is used to eliminate undesired modes in the current drive circuit, 107 to a drive amplifier, 108 and closes the loop to drive the sensor drive winding, 109, with drive currents which as synchronized of amplitude and phase to achieve and maintain a stable sensor motion. Since the resultant motion is essentially sinusoidal about the sensor null position, and the back EMF is proportional to the velocity of motion, then the amplitude which is referenced to 104 is the sensor velocity. The frequency waveform generator, 110, provided for off board signal processing to measure the sensor frequency (or period) of oscillation since the fundamental output from the comparator of the sensor elements is a pulse stream at the sensor resonant frequency.

The detection circuit, 103, can be either a peak detector or average waveform circuit. The circuitry to implement an average waveform circuit peak detector uses all the available waveform and the result is not sensitive to waveform distortion. The peak detector approach has minimum filtering delays and either approach can be utilized.

Figure 22:
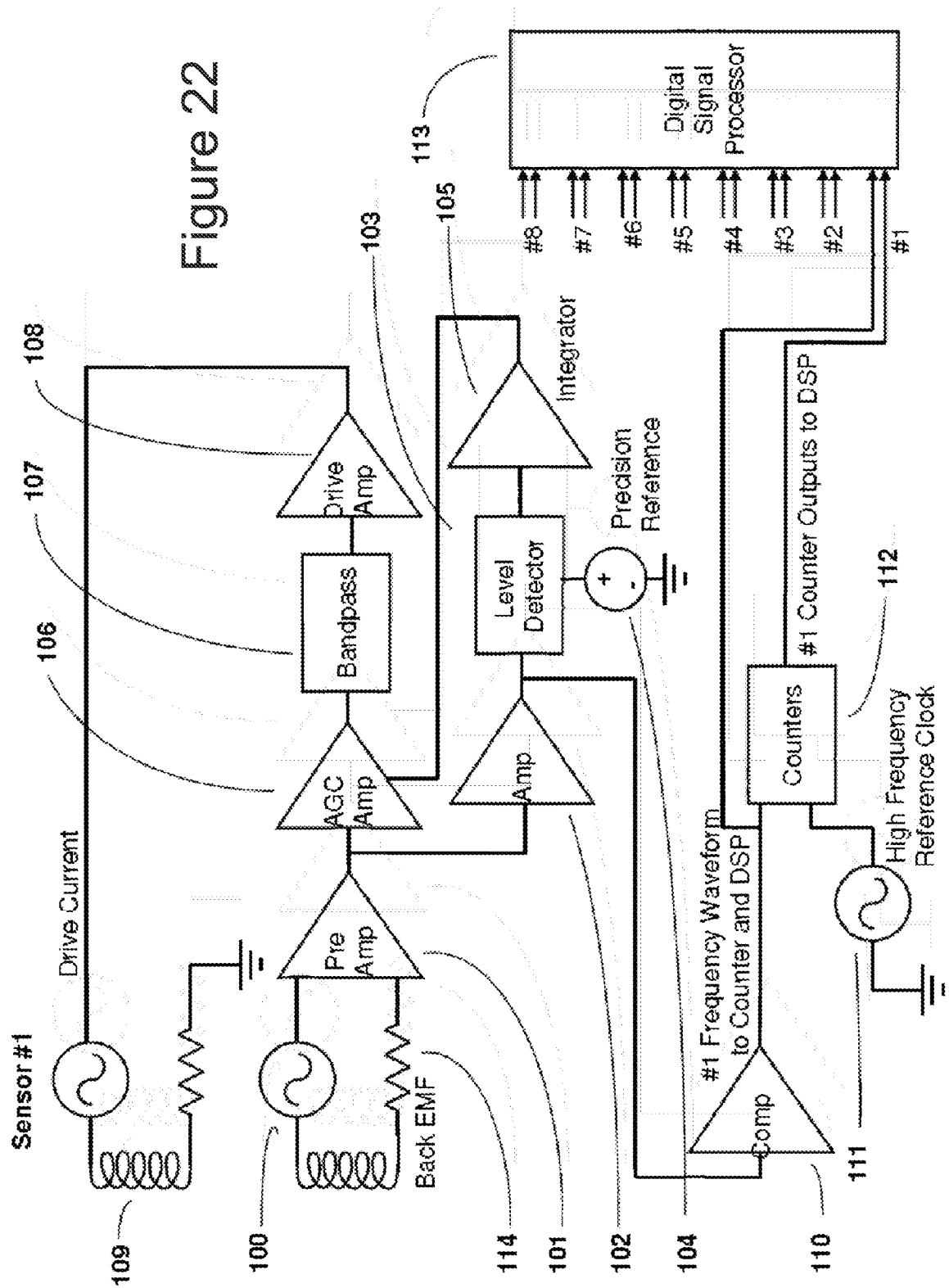
FIG. 22 is a typical signal processing circuit utilizing discrete counters.

FIG. 22 shows the addition of a separate counter, 112, triggered by the comparator, 110, for counting high frequency clocks, 111, to measure the sensor frequency or period of oscillation by converting the count for a period to a digital word. Both sensor period data and count clocks can be input into a DSP/FPGA, 113, for accurately determining the sensor period from which the added mass for chemical detection can be calculated. Alternatively, the counting function can be placed in the DSP if the DSP is fast enough to process the counting function. External counting relieves the DSP from the requirements of high speed and permits use of a low power device such as the TI 430 DSP.

For the external to the DSP counting approach, if a 2 GHZ clock, 111, is gated by a 50 KHz sensor signal from the comparator, 110, this count is 1 part per 20,000 or 11 bits of data. The method of counting can be as outlined or based upon time stamped level crossings for either a digital or analog based implementation. With a sensor scaling of 10% frequency change for full scale, this is 2000 of useful data evaluable in a period of every 100 usec or with over sampling in 100 msec we approach $2 \cdot 10^6$ or 21 bits of resolution. Note, that there is a fundamental sensor-electronics trade-off because if the sensor resonant frequency were to be dropped by an order of magnitude from 50 KHz to 5 KHz by changing sensor design parameters while increasing the amplitude of oscillation by an order of magnitude, then the velocity back EMF sense signal amplitude at resonance is still the same, but the resolution of the frequency sampling has been improved by an order of magnitude. This is a possible design optimization approach limited by the noise interference from acoustic energy, mechanical stress in the sensor and mechanical noise terms. Those skilled in the art will know that a phase lock loop can be added to the output of the comparator, 110, between the counter, 112 for reducing the noise of the signal.

FIG. 22 shows the signal from more than one sensor can be processed at a time. Each sensors frequency is unique and requires separate tracking circuits of items 100-110, and 112 implemented as individual circuits or as ASICs. The processor 113 can be duplicated as well or a signal high speed processor can be employed. A common high frequency clock, 111 can be used. A high speed processor could be a TI ARM AM3517 DSP which runs at 500 MHZ or it could be an FPGA based counter approach using the Virtex-6 which is capable of 11.2 Gb/sec communication operation.

Those skilled in the art will note that the sense signal shown as a back EMF signal can be replaced by a PZR sense driven by a precision dc low noise current source that generates a sense signal that can be used similarly. The BEMF sensor is replaced by a piezoresistive (PZR) sensor constructed by ion implant of the stiffness leg of the sensor through ion implant e.g. boron to form a resistance that is stress dependant. The idea is that a precision current source passes a dc current through the PZR and the resultant voltage is filtered to remove the dc level and measure only the stress induced ac voltages as the sensor oscillates. This approach has the advantage of providing a signal at even low frequencies for detection of the resonant frequency signal and for providing a large signal. The Johnson noise of the PZR sense resistive element must be considered in the noise model and compared with the ohmic sense resistance, 114, in FIG. 22.

Figure 23:
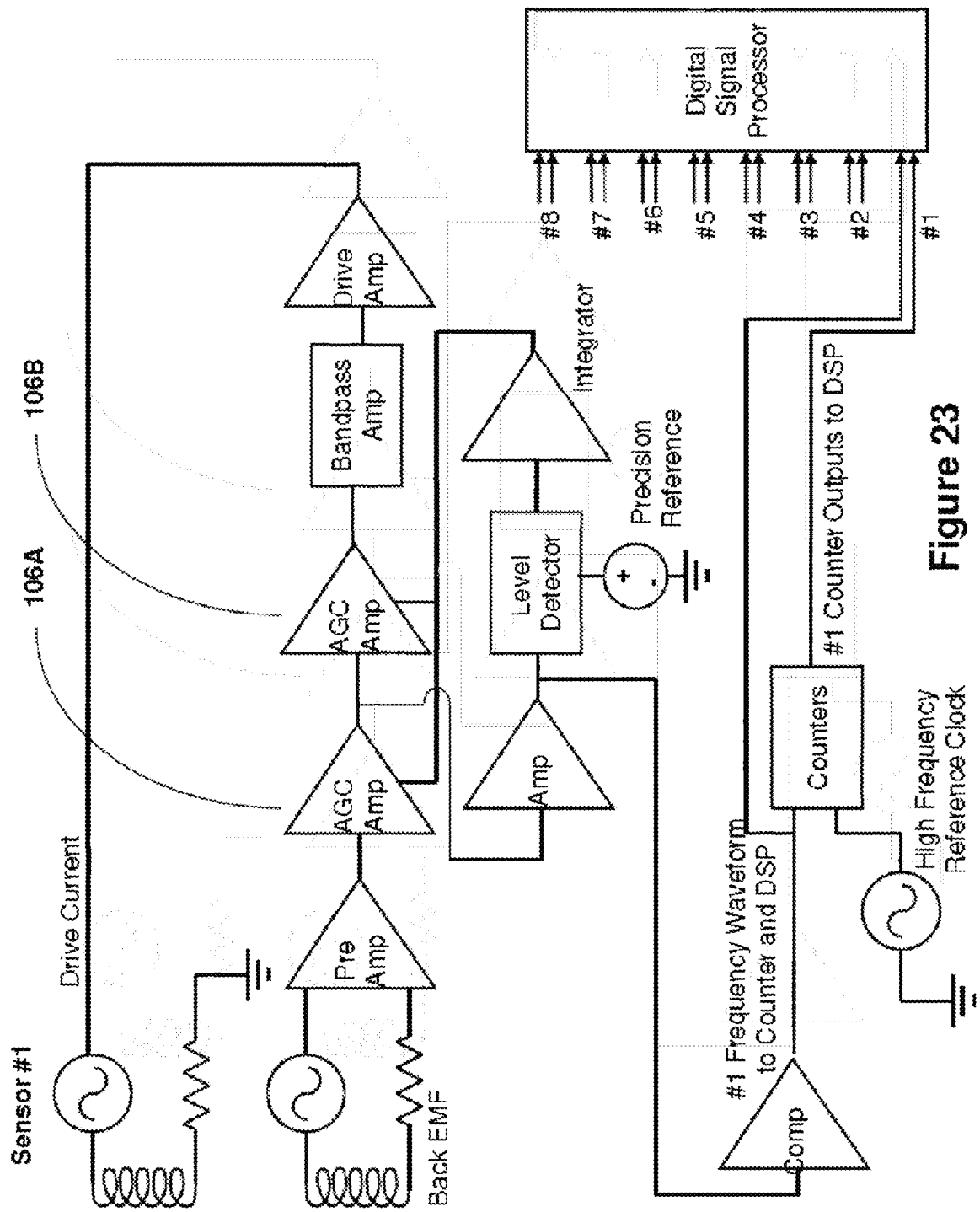
FIG. 23 is a block diagram of the analog control electronics.

The FIG. 23 a shows the same block diagram as for FIG. 22 of a complete analog based system from end system with the DSP providing the processing for multiple sensors. This circuit shows the added compensation to account for permanent magnet aging and temperature The AGC gain block 106 is replaced with two cascaded blocks 106A and 106B is to compensate for the sensor scale factor change and the drive current-to-force transfer function as the magnetic field changes. The DSP also uses over sampling to reduce the noise level.

Figure 24:
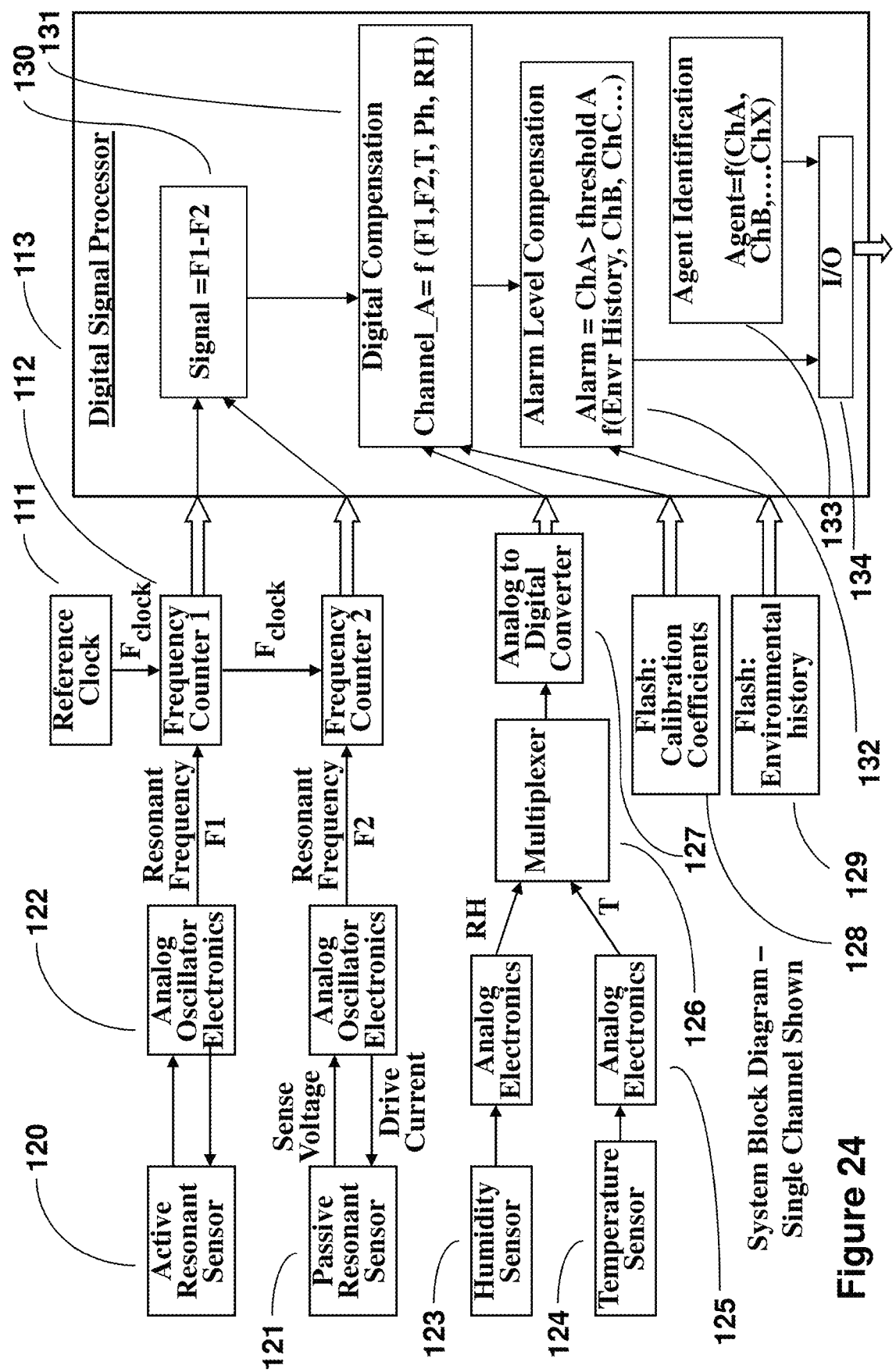
FIG. 24 is a flowchart of processing of the frequency signals and compensation techniques.

One approach to processing signals from the active resonant sensor, 120 and reference resonant sensor, 121 is shown in FIG. 24. This illustrates the processing of the detection signal based upon a two element subset of the sensor array. This system employs independent frequency counters, 112, gated clocks pulses, 109, from the analog oscillator electronics, 122, and with synchronized sample timing that may be external to the DSP, 113 as depicted or internal to the DSP as discussed previously. One of the sensors is called the passive or reference sensor, 121 which has minimal response to the chemical of interest and the other is a sensor with the detection coating for a maximal response which is referred to as the active sensor, 120. What is being described is directly applicable to a multitude of active sensors in an array with more than one active resonant sensor or even more than one reference sensor. The use of the passive sensor when combined with the active sensor in signal block, 130 of the DSP, 113 is used to eliminate common mode effects such as pressure changes, external vibration effects, humidity, contamination or common temperature effects in the DSP 113. Each sensor has a nominal resonant frequency at a given starting point that has been calibrated and changes with parameters such as temperature, and humidity that can be sensed. Temperature sensing 124 and 125 can be used to compensate for any sensor changes in frequency or for electronic temperature effects in DSP block 131. Initial values of calibration coefficients, 128, and history, 129 can be supplied from flash memory of provided to the DSP at initialization through the I/O, 134. Similarly humidity, 123 or pressure which is not shown is used to counter any frequency changes caused by them. The input of this information can be as described through blocks 123, 124, 125, 126, and 129 or the sensors may be I2C and be linked to the DSP through a serial bus. Changes of frequency from the nominal for each sensor are compared after correction for these inputs and the frequency difference attributed to the active sensor is extracted.

The calculated information from the digital compensation, 131, is assessed and filtered in the alarm level compensation block, 132 and agents identified 133 for output to the user, 134.

A notional signal processing algorithm for a sensor, which compensates for temperature, humidity, and pressure, is shown below:

$$Signal = A_0 + A_1*T + A_2*T^2 + A_3*T^3 + B_1*(f_1-f_2) + B_2*(f_1-f_2)^2 + B_3*(f_1-f_2)^3 + C_0*P + C_1*P*(f_1-f_2) + D_0*H + D_1*H*(f_1-f_2) + E_1*(f_1+f_2)$$

Where the terms are defined as:
$f_1$ = Reference resonator frequency
$f_2$ = Active sensor resonant frequency
T = Temperature in kelvin—295
P = Pressure-Atmospheric at sea level
H = Relative humidity in percent—50%
$A_0$ = Bias offset term
$A_1$ = First order temperature sensitivity of bias offset term
$A_2$ = Second order temperature sensitivity of bias offset term
$A_3$ = Third order temperature sensitivity of bias offset term
$B_1$ = First order temperature sensitivity of scale factor term
$B_2$ = Second order temperature sensitivity of scale factor term
$B_3$ = Third order temperature sensitivity of scale factor term
$C_0$ = First order pressure compensation term
$C_1$ = Second order pressure compensation term
$D_0$ = First order relative humidity compensation term
$D_1$ = Second order relative humidity compensation term
$E_1$ = Compensation for common mode frequency related errors This compensation is also applicable to the digital signal processing approaches discussed below in which the frequency counting is either performed in separate ICs or are integrated with the DSP function.

Digital Signal Processing System:

A digital signal processing implementation has the adds the capability for flexible digital filtering, over sampling for low noise floors, narrow pass band filtering for a low noise floor, vernier closed loop phase control, controlled operation of sensor amplitudes, ease of multiplexing, self calibration, and thermal control by dc current injection. The concept is to detect the sensor signal and digitally processing it to drive the sensor at the same frequency so they are locked together and perform the period counting operations for an array of sensors for one to eight in the present implementation. When the sensor sense and drive signals are locked in phase and frequency, the most efficient operation and the lowest power is when these signals are locked together such that the current waveform applied to the sensor drive coil against its electromotive force (EMF) is in phase with that from the sense coil. With this digital approach we are using we will locate and lock onto this lowest power point for most efficient operation and lowest power.

As in any resonant device, it is really the damped frequency that is sensed but since the Q of the sensor is high, of the order of 5,000 for these discussions and the resonant frequency is of the order of 50 KHZ depending upon which sensor is considered in an array. Then for a sensor modeled as a linear second order damped spring, mass system the sensor damped frequency is calculated from the product of the undamped frequency and the square root of one minus a parameter depending upon the reciprocal of the square of Q. These frequencies are nearly identical so small changes in Q are typically very small. However, with this digital approach even these small effects can be corrected in the digital processing of the signal. In addition, parametric evaluation of changes relating to the effective spring rate and effective mass can also be modeled processed in digital processing to extract the useful sensor signal for chemical detection.

Figure 25:
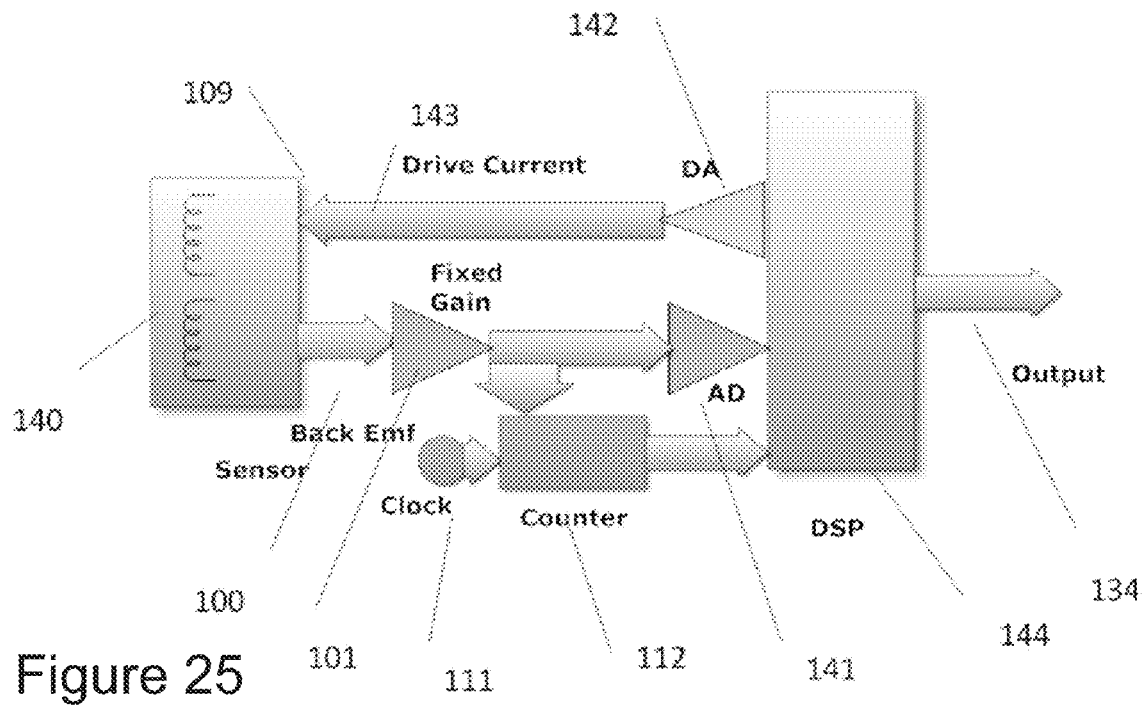
FIG. 25 is a flowchart of digital control electronics with gain stage and digital-to-analog convertor drive.

The closed loop system of FIG. 25 could be implemented with a low noise amplifier followed by an AD converter to digitize the amplified sensor back EMF into a digital processing function implemented in a processor, field programmable array (FPGA), or application-specific integrated circuit (ASIC), 144 containing the desired algorithms. More generally, the system includes a processor having a memory possessing algorithms. As will be described in more detail, the sensor drive would then originate from this processing function with a DA converter to command the desired current. Another purpose of the digital processing function is to measure the frequency that the sensor is resonating at provide this as an output signal. Over sampling techniques, temperature correction, and individual sensor unique corrections are applied before outputting data. The high speed counting associated with measurement of the sensor frequency, could be done in a high speed DSP e.g. Arm AM 3517, but this would push the sensor frequency considerably below 50 KHz for this ADC and DAC implementation, an external period counter circuit is used as already described in the analog section of the document.

In FIG. 25, sensor back EMF 100, which comes from the sensor block of a sensor array 140, is amplified by a low noise amplifier 101 and has a nearly sinusoidal waveform which is digitized by the ADC 141 and fed into the DSP, FPGA, or ASIC controller, 144. The ADC sample rate is selected to retain the ability to reconstruct the basic waveform for control of the synchronous sensor drive waveforms and for a period counting functions. The sample rate can controlled depending upon the criticality of the waveform determination and can be as low as about 8 counts per cycle for determining driving waveform only but much higher is crossing and phase information is required. The crossing information can be determined separately by generating a comparator derived signal, 110 described earlier. The controller, 144 controls the amplitude of the sensor oscillation by commanding synchronous amplitude of voltage or current through an amplifier, 143, with the digital to analog converter, 142, which drives the sensor drive, 109 such that if the sensed amplitude is lower than desired, the amplitude of the command will be increased to compensate as in a normal compensated digital closed loop mode and lower the command amplitude if the signal is too high. The high Q of the sensor acts as a filter so that the DAC points per cycle required can be reduced which minimizes the computation load The DAC points per cycle can be increased or decreased depending upon the sensor processing load and sample detection accuracy required. The sensor control requires a modest closed loop frequency response which is lower than that for the detection of the resonance in the range of about 40 KHz to 60 KHz because of the high Q of the sensor. This implementation has an external counter, 112, with a high frequency clock, 111, which is gated from a comparator supplied from the preamplifier 101 for detecting the sensor period of oscillation. The output of 156 is the period measurement data which is supplied to the DSP or FPGA, 144 for processing which provides processed data, 134, for either operator I/O or for higher level processing algorithms.

The advantage of using the AD converter, 141, is that the entire waveform is captured and can be processed, but the disadvantage is the limitation on high speed AD's and the corresponding power penalty for digitizing the entire waveform. As an example, 24 bit AD 7762 sigma delta converter which runs at 0.625 Msps is not fast enough to fully capture the sensor waveform. Simplifications are possible since we are driving a high Q resonant sensor whose output is nearing sinusoidal and the waveform can be sampled at known points in the cycle. E.g. peaks of the waveform to form a digital peak detection circuit or multiple samples to determine the average waveform. Similarly, a DA converter, 154, may be replaced by less complex drivers because of the filter effects of a high Q sensor which attenuates drive harmonics other than the fundamental. Note, in all the simplified circuitry a low noise analog amplifier, 101, is necessary to boost the sensor signal to usable levels.

Figure 26:
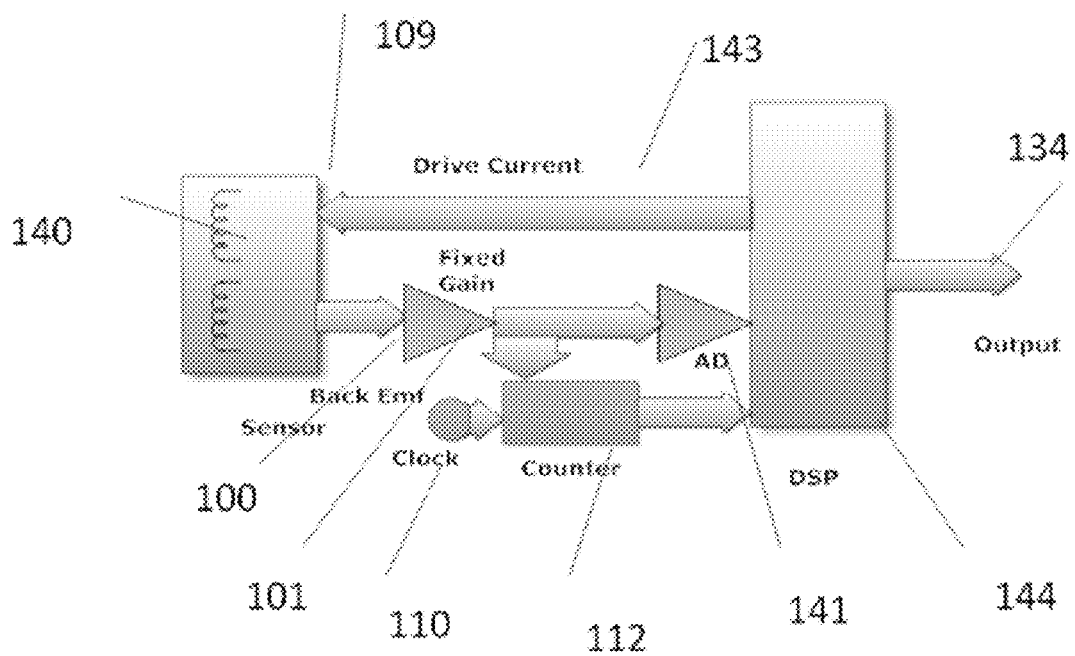
FIG. 26 is a flowchart of digital control electronics with direct drive from DSP/FPGA.

Before going into ways of simplifying the AD and counting functions, we will address the means of simplifying the creation of the driving the current in FIG. 26.
(i) Reducing the period of conduction to less than 180 degrees per ½ cycles by symmetrically turning the coil on later and turning it off earlier
(ii) Driving the coil n cycles every m cycles where m>n where m is an integer.
(iii) Apply a PWM modulation to the waveform.
(iv) Apply an amplitude level control through an H bridge type of driver The preferred drive is with the waveform width control which is power efficient by supplying power near the peak of the back EMF with low noise waveform as compared with a PWM drive signal since there are only four switching edges per cycle. Waveform width control substantially eliminates all even harmonics and is very efficient because current flow is commanded near the peak back EMF.

Figure 27:
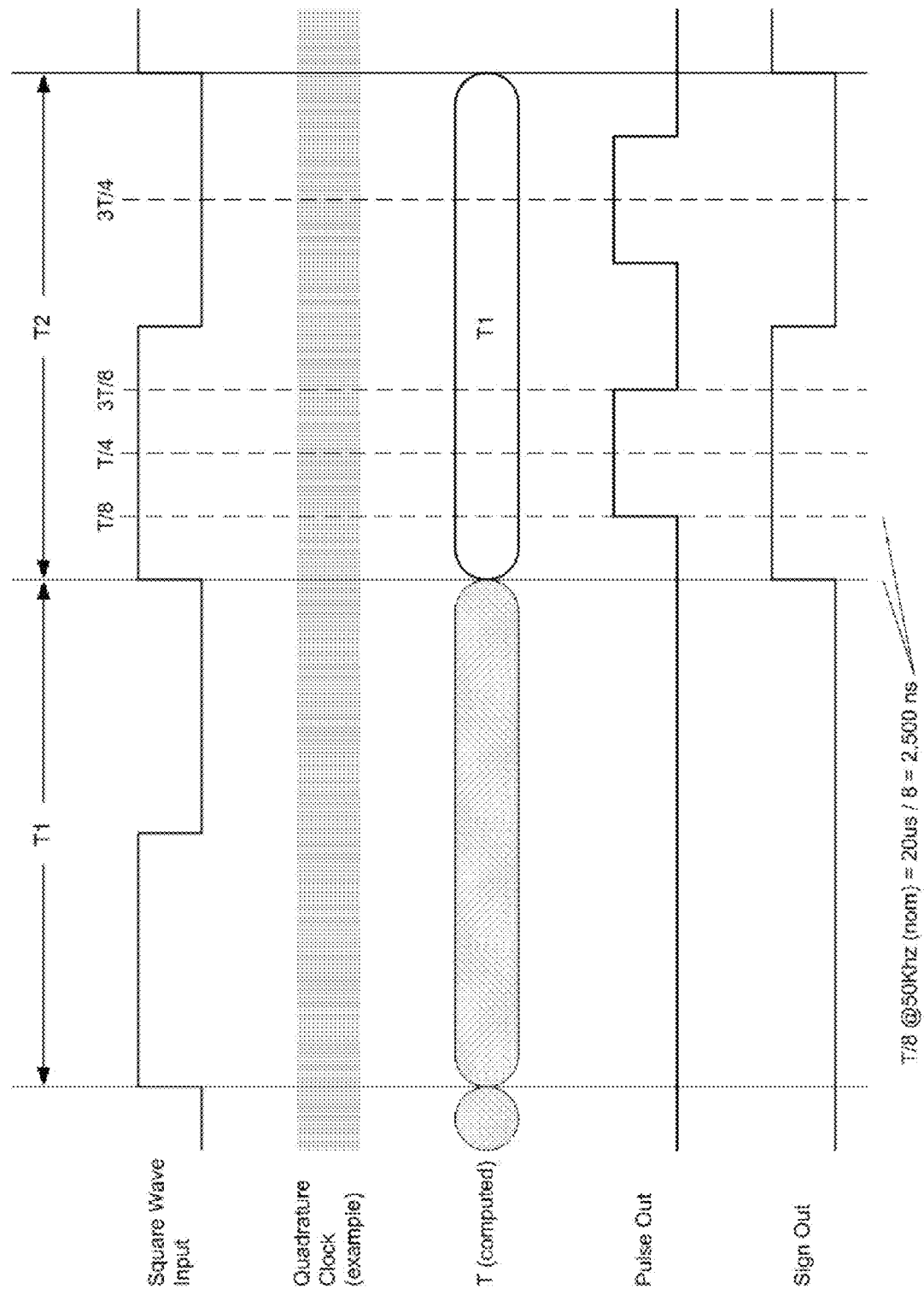
FIG. 27 is an event timeline of digital control electronics with preferred direct drive waveform from DSP.

An example of the direct drive waveform for the preferred drive approach is shown in FIG. 27.

This waveform width control drives the sensor with frequency and phase coherence to the sensor back EMF. The drive waveform which is shown when the sensor is being accelerated varies from a full on interval, here depicted as starting at T/8 and ending at 3T/8 for the positive portion of the drive waveform. These points are selected in advance e.g. T/8, 3T/8, 5T/8, and 7T/8 and are chosen for maximum power efficiency, and best noise cross coupling performance with the sensing windings where T is the period. These points can be adjusted to that maximum drive can be moved to 0, T/2, and T as needed. The circuitry can be either current command or in the present implementation of a voltage driven source e.g. S1998 or OPA 564 which allows inhibiting the current flow from the driven back EMF to maintain the high Q operation during the off portion of the waveform drive.

Figure 28:
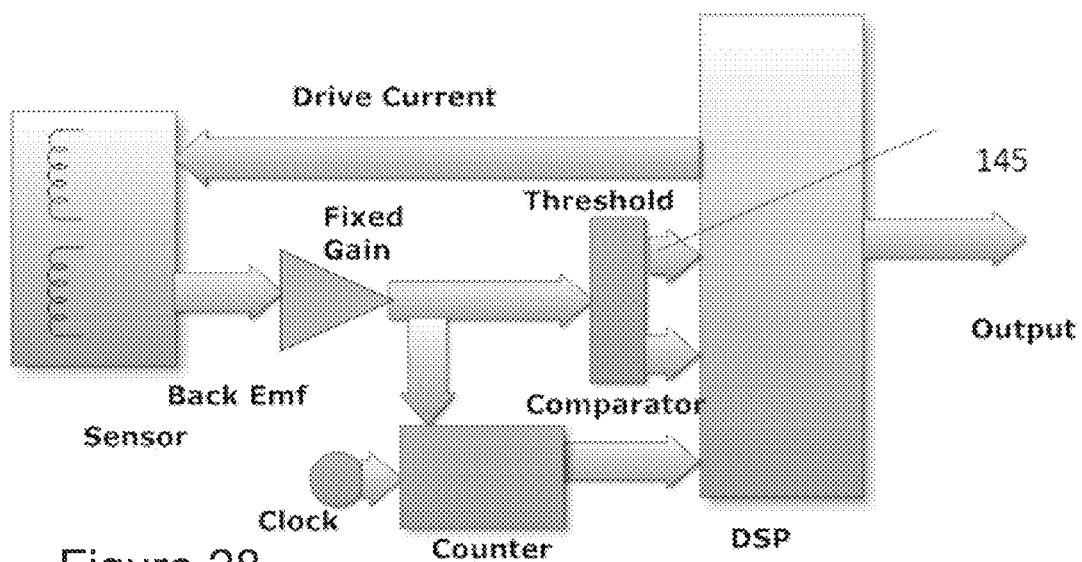
FIG. 28 is a flowchart of a simplified threshold detector replacing ADC with digital control electronics.

Next, in FIG. 28 we show a configuration in which the AD converter, 141, of FIG. 26 is replaced by simpler logic elements, 145. The FIG. 28 excludes the DA converter and uses one of the drive options discussed above but it could be configure in a version with a DA converter. The approach is to use a comparator to square up the sensor sinusoidal waveform so that the processing function can directly perform a high frequency counting operation of the sensor resonance frequency. Also, adjustable logic, 145, is selected from the processing function which takes the rectified average amplified voltage from the sensor and compares it to a desired level. If the resultant logic signal is too low than the drive signal is controlled to increase it and if it is too high as indicated by the logic, then the drive is reduced in a controlled manner. The period counter shown in the implementation can be as shown, that is external to the DSP/FPGA function, or internal to the FPGA/DSP function. This loop runs at a much lower frequency than the basic counting loop. In this implementation there is one DSP, one clock, and power supply for all sensors in the array and each sensor has its own counter, fixed gain amplifier and threshold comparator circuitry in the basic implementation that is capable of running sensors simultaneously. Because of the high Q of the sensors, multiplexed sensor operation is possible at the expense of the signal to noise ratio, and is not selected for the baseline for the highest sensitivity chemical sensor.

As in any resonant device of this nature, initiation of the closed loop tracking is necessary to maintain the desired amplitude as at start the sensor is at rest and must be made to oscillate at it resonant frequency. Since the sensor signal, 100, is zero at rest there must be a means of perturbing it to generate a back EMF signal. Impulse or step disturbances do not introduce enough energy to cause this to happen in an efficient manner. A fast Fourier transform (FFT) to pick out the signal from the noise is possible once sufficient back EMF signal can be detected by the ADC, 141. Efficient starting is by introducing a novel slow varying sweep of drive with a chirp signal starting below and near the expected resonance and increasing to above the expected frequency. What we rely upon is the high Q filter effect of the sensor since it filters frequencies and only responds at the resonant frequency. A satisfactory start up mode to start a preparation for sensor period detection is detected by a combination of period counting signals near the expected period in combination with sensor velocity information near the expected resonant frequency and exceeding a threshold value. As in any resonant device of this nature, initiation of the closed loop tracking is necessary and will be discussed in another section.

Figure 29:
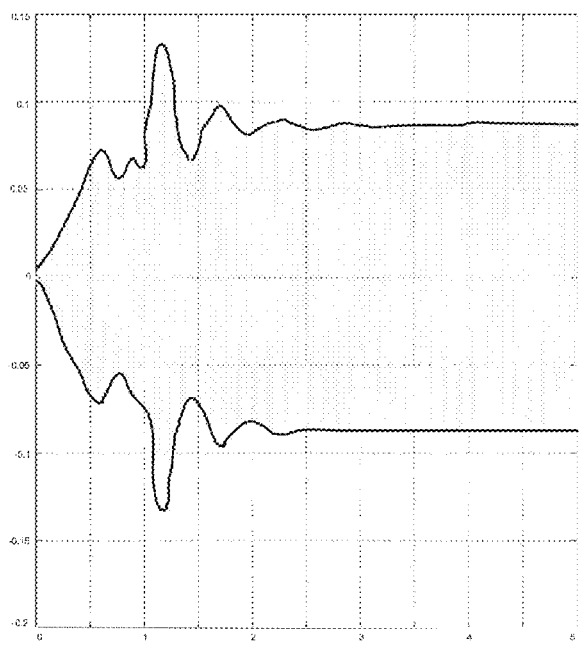
FIG. 29 is a graph showing digital loop startup sensor dynamics.

Starting and locking onto the rate signal generated by the sensor are straight forward with this chirp driven loop. As will be illustrated shortly with a MATLAB simulation, the startup operation of the simple digital loop is also straight forward. The approach of using an open loop swept drive waveform in a mode called the Chirp state driven from the DSP, 144, with frequency, f1, starting below the expected range of the resonant frequency, f0, and then increasing towards and above the expected resonant frequency, f2 in sweep time, and tsweep of the sensor is shown in FIG. 29.

Figure 30:
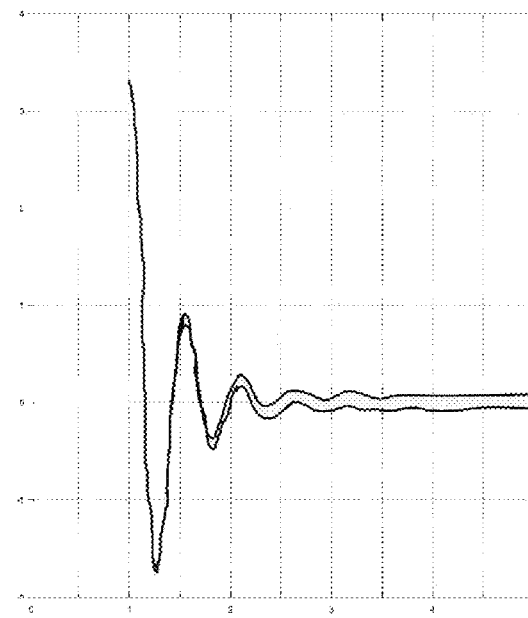
FIG. 30 is a graph showing digital loop startup dynamic velocity error.

The time scale is in msec and the vertical scale is in sensor units. The plot shows that after about a msec, the sensor amplitude is sufficiently high that the closed loop has begun and the processor is in full closed control and tracking the sensor frequency with only small errors after about 2.5 msec as illustrated by the error plot of FIG. 30. The Chirp state is only terminated when the threshold criteria are met and the controller moves to the closed-loop state.

The goal of the closed loop state is to use a closed-loop PID controller method to efficiently move the sensor into the desired resonance amplitude in the shortest time without excessive overshooting of the desired amplitude. If sufficient amplitude is achieved the sensor commands may be placed in the Coast Mode for quiet period measurement without the noise of a driven waveform if desired.

Figure 31:
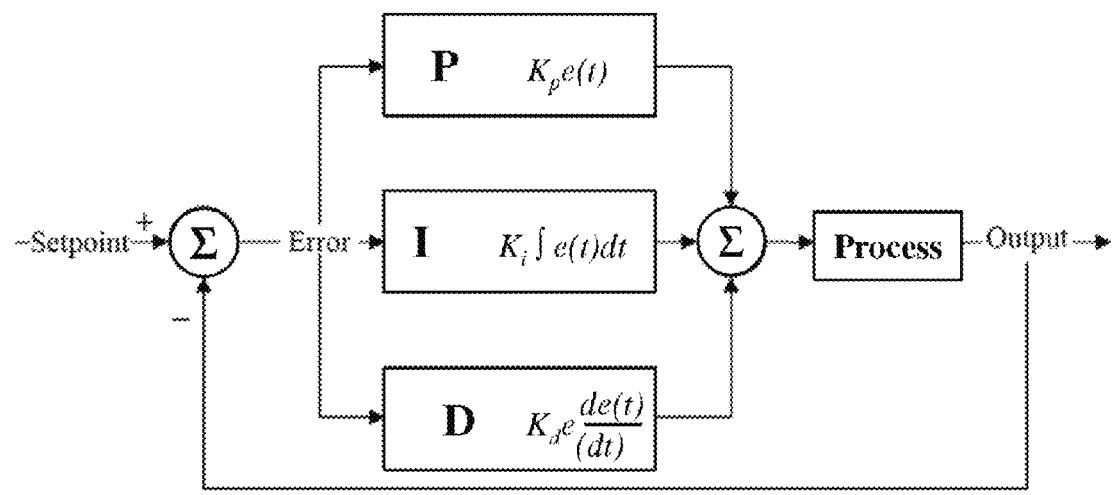
FIG. 31 is a flowchart showing a closed loop velocity controller.

The input to the PID controller shown in FIG. 31 is an amplitude error based on the difference between sampled values of A and a temperature-dependent target value of A associated with the specific sensor. This target value indicates when a sensor is at the desired resonance amplitude for a given ambient temperature and is obtained via characterization. The output of the PID controller is a value "K" that is combined with the current value of T to determine the width and of a pulse waveform to form the closed loop. The inhibit command of the drive power amplifier is removed and separate drives for positive and negative waveforms are applied. Previous FIG. 27 shows the pulse waveform is used to drive the sensor's input drive coil and which must be done in-phase with the square wave coming from the sensor. This is shown for maximum drive and acceleration.

The closed loop velocity controller is shown in FIG. 29 converts the difference in desired velocity (e.g. desired displacement amplitude peak after correction for frequency) to measured frequency. The velocity amplitude can be input into the PSP/FPGA by several means:
 (i) External sensor back EMF peak detector circuitry which is sampled by an ADC for input into the FPGA/DSP
 (ii) External sensor back EMF rectification detector circuitry which is sampled by an ADC for input into the FPGA/DSP
 (iii) External sensor back EMF detector which is sampled at the correct time to determine the peak value.

Initially, the parameters can be selected for rapidly reducing the error signal to get close to the desired frequency not unlike that of a GPS system in the acquisition mode. As the signal is acquired more accuracy is required, the tracking band width can be narrowed to reduce the background noise and improve accuracy.

The purpose of the closed loop control is to maintain an adequate level of signal during the measurement portion of the cycle. The displacement amplitude of the sensors needs to be a large value for best S/N ratio, but not so large that MEMS elements such as the legs of the sensor are over stressed which could lead to sensor breakage. This is done by establishing a set point commanded velocity. For a given maximum displacement of the sensor, D, as determined by design and for a given sensor velocity, w, then the back EMF is proportional to D*w. Therefore, after characterization of the sensors, each set point velocity can tailored to a sensor correcting for its actual resonant frequency to maintain D in the DSP/FPGA, 144.

The back EMF signal is also a function of temperature because of effects dominated by magnet field fall off with increasing temperature. The temperature of the sensor is needed to properly compensate for any temperature related temperature changes. The electronics, 144, can control this sensor whether we set its nominal frequency to 50 KHz or to a lower value. If conventional sensors are use, their signals would be brought into the processing core as needed.

The instability of the magnet over time and temperature is a potential error contributor and can be compensated for in the DSP, 144. As the magnetic field increases perhaps due to being colder, in an uncompensated loop, the back EMF sensed that the pickoff measures excess amplitude and the loop would tend to reduce the drive level. This can cause a change in frequency due to the amplitude-frequency sensitivity deriving from third order non-linearity in the flexure suspension. This error can be mitigated in several ways. First, the system is calibrated as a function of temperature, so temperature sensitivity error is reduced by an order of magnitude or more. Secondly, a magnetic field sensor can be employed to compensate for B field changes. This sensor must be more stable than the magnet drift error. It is possible to build this sensor into the MEMS device. This sensor will compensate for both aging and temperature effects. A third approach is to use an increased gain in a velocity amplitude control loop. The preferred approach is to adjust the commanded set point.

Figure 32:
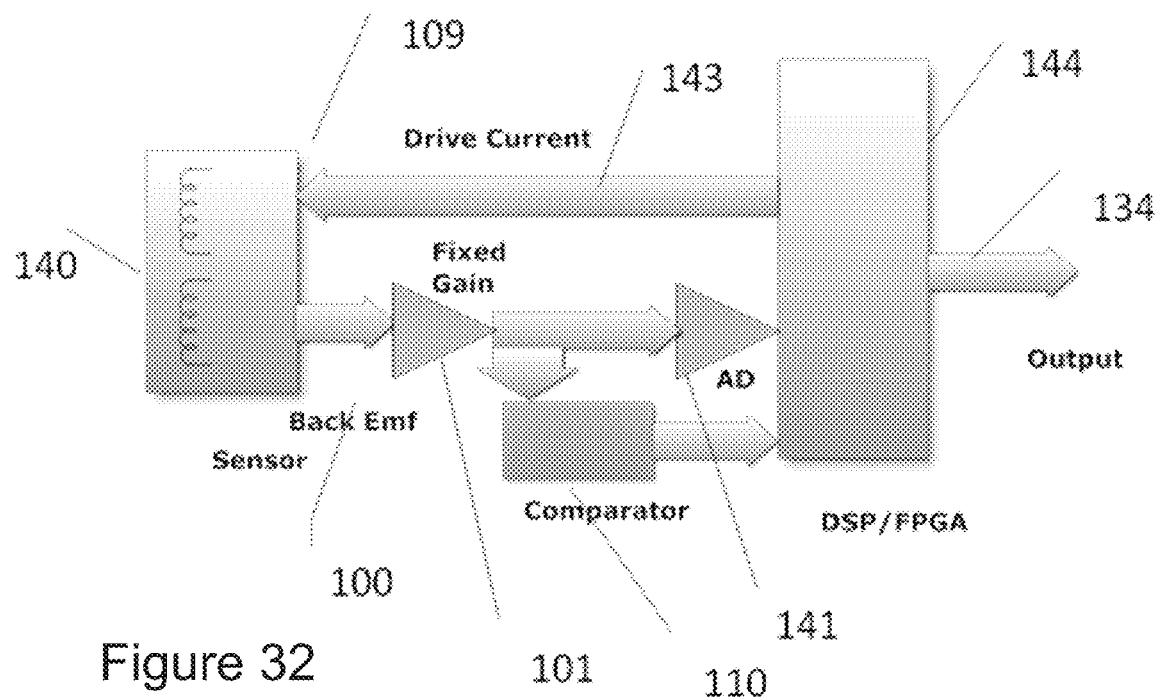
FIG. 32 is a flowchart showing a preferred embodiment of DSP/FPGA electronics.

Another trade involves multiplexing of the sensors versus providing individual control electronics for each resonator. The multiplexed system has the advantages of lower cost, lower power, smaller size, and less crosstalk between channels. The disadvantages include lower performance due to switching transients, reduced sampling time by nominally one over the number of resonators, inability to do no-lost-count sampling (reducing noise by a factor of $1/N^{0.5}$ instead of $1/N$), sample time lost while the resonant amplitude stabilizes, Next we describe the preferred embodiment in FIG. 32 in which the electronics is kept to a minimum and most digital processing occurs in an FPGA or DSP, 144, after appropriate level shifting for different voltage levels. This implementation relies upon hardware electronics that adds a low noise, fixed gain amplifier, 101, to increase the sense signal, 100. A representative low noise instrumentation amplifier is the AD8429. The input sense signal is then fed to a fast low noise comparator, 110, with selectable hysteresis level e.g. ADCMP601 which provides the squared waveform used for period measurements in the fpga, 144. The fpga determines when level shift from low to high or high to low with truth table driven logic to debounce the change in state. A measurement function occurs in the FPGA/DSP processor, 144, such as the Xilinx Spartan 6 which precisely measures the time interval coming from the comparator with a high frequency clock. This measurement consists of redundant counters operating of both the rising and fall edge of the comparator edges combined with voting logic to eliminate data not required for the computations. Both long counters and short counters are used for the period measurement critical to the chemical detectors output. The long counter is used to determine the period results with continuous over sampling over an interval of seconds. The short counter determines the basic timing so that the sensor drive waveforms, 143, discussed prior to this in FIG. 27 are synchronized to the sensor drive input, 109 since the sensor and drive back EMFs are essentially in phase, The velocity information is measured by a fast ADC, 141, such as the LTC 1850 which is synchronized to the gained sense back EMF signal for measurement at the T/4 or 3T/4 points of the waveform, e.g. the positive or negative peaks. This novel peak detection is used to minimize the delays that would be involved sampling a rectified and filtered waveform. The ADC also multiplexes up to 8 sensors, 140, for processing in the FPGA, 144, and outputting the results of the period measurement, 134.

The drive waveform implementation, 143, is as described in FIG. 27, and is controlled from the FPGA, 144, to drive the sensor, 109. Spatial separation of driven sensors can be used to minimize cross coupling in the sensor array. When a measurement cycle is not in process for a particular sensor in the array, the sensor driver can be commanded to be an essential short at the sensor thereby providing a path for sensor induced currents to help damp vibrations and coupling motion.

After the sensing cycle is complete, the sensor can be allowed to coast to rest by putting the sensor driver in a high impedance mode, driven synchronous to the sensor to command deceleration closed loop to toward rest to remove most of its kinetic energy, or have the sensor driver shorted to cause dynamic braking aid in the deceleration toward rest. The last two reduce the time the sensor is in motion, and sensor to sensor coupling effects-noise, vibration.

Figure 33:
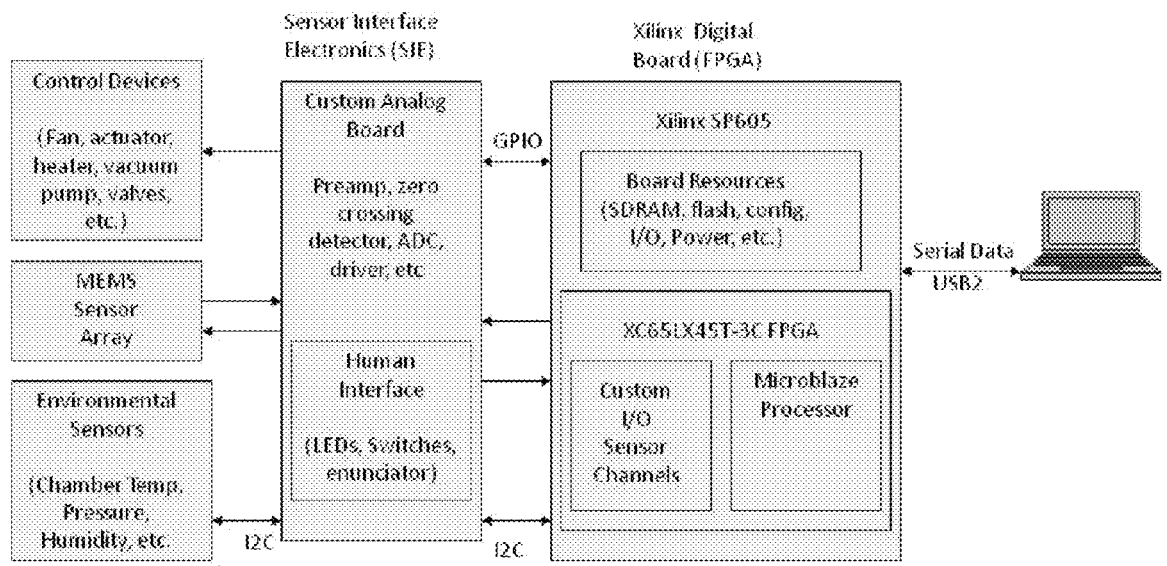
FIG. 33 is a flowchart showing implementation including an external PC for data processing of algorithms.
Figure 34:
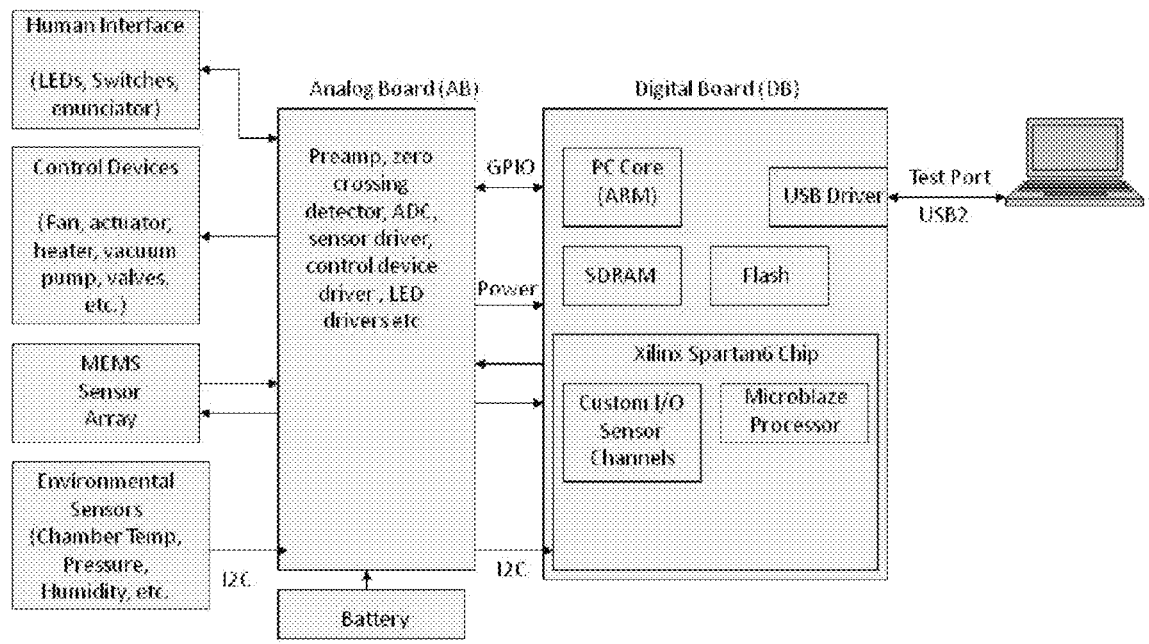
FIG. 34 is a flowchart showing implementation including internal data processing of algorithms.

A block diagram of the system is shown in FIGS. 123 and 124. The system is based on the use of a novel MEMS sensor whose resonant frequency can be used to uniquely identify a substance that is introduced in a chamber and deposited on an array of MEMS based sensors. At the heart of the system is a rapid response real time controller that controls and acquires data from eight of the MEMS sensors. This is the measurement and control functions we have been discussing. In addition, the controller is responsible for data acquisition from various slow changing environmental sensors as well as control of various devices such as fans and heaters. Two implementations are presented. The first configuration is shown represented with a FPGA development board (FPGA) mated to Sensor Interface Electronics (SIE) and a PC as shown in FIG. 33. The other configuration shown in FIG. 34 consists of a digital architecture containing both the PC functionality and the FPGA in a Digital Electronics (DE) board. The controller is implemented in the FPGA contains: (1) a custom soft embedded processor subsystem (Microblaze) and, (2) a custom IO peripheral. The custom peripheral resides on the processor's IO bus and assists with controlling the MEMS sensors and acquiring data from them. The custom peripheral internally consists of up to eight "sensor channels" or control/data paths, one for each sensor in the system. The analog interface board (AB) could be modified by moving interfaces off the analog board and into a package exterior.

In the alpha configuration, the operator interface is a standalone PC which communicates with the controller using a serial data link. Commands can be issued to the controller from the PC and measurement data can be downloaded off the controller to the PC for archiving. The PC also hosts the analytical software that performs the materials analysis described later.

While the invention has been described in its preferred embodiments, it is to be understood that the words which have been used are words of description and not of limitation. Therefore, changes may be made within the appended claims without departing from the true scope of the invention.

What is claimed is:

1. A system for detecting one or more target chemical compounds, comprising:
   an array of one or more resonant sensors each comprising:
      a mechanical spring-mass system employing:
         a thin planar structure lying in a plane and having a damped natural frequency and comprising:
            two motional masses spaced apart along an X-axis in the plane and dynamically linearly balanced along the X-axis and suspended by two or more spring suspension elements extending in a Y-axis in the plane from the masses to a surrounding frame, with the spring suspension elements having a cross-sectional geometry that results in substantially higher stiffness to out of plane motion than X-axis motion to constrain the masses to substantially linear resonant motion in the plane of the thin planar structure while minimizing motion out of the plane, the masses further being connected by a linkage disposed therebetween constraining them to move linearly 180 degrees out of phase with each other along the X-axis and substantially constraining both masses from moving together side-to-side along the X-axis, wherein the linkage comprises flexible beams that connect both to the frame and to each motional mass, and wherein the flexible beams define an elongated diamond shape having a first pair of opposite apexes connected to the motional masses along the X-axis and a second pair of opposite apexes connected to the frame and spaced apart farther than the first pair; and
         an active coating on or in the motional mass with an affinity to capturing or reacting with the target chemical compound in order to change its own mass in response to the presence of the target chemical compound and affect a change in the damped natural frequency of the thin planar structure;
      drive electronics to control the amplitude of a driven resonant mode of each sensor in the array at its damped natural frequency;
      a signal processing system to detect a change in a damped natural frequencies or periods of the one or more sensors; and
      a processor including a memory possessing a set of algorithms to convert the detected change to an indication of target chemical detection.

2. The sensor system of claim 1, wherein each spring suspension element comprises multiple thin flat beams having a length in the Y-direction a height in the Z-direction substantially greater than a thickness on the X-direction.

3. The sensor system of claim 1, wherein the signal processing system receives input from a sensing surface area in which the sensing surface area-to-motional mass ratio is improved by forming holes comprising:

a plurality of hexagonally shaped holes through the thin planar structure in a normal direction to the motion of the sensors.

4. The sensor system of claim 1, wherein the signal processing system receives input from a sensing surface area in which the sensing surface area-to-motional mass ratio is improved by using an open porous structure in the sensing area.

5. The sensor system of claim 1, wherein the array has multiple sensors with one or more having different active coating types, and further including:
electronics to provide chemical detection and compound identification based upon a signature of frequency changes for the different active coating types.

6. The sensor system of claim 5, wherein:
the multiple sensors are slightly offset in frequency to allow simultaneous operation with reduced potential for cross coupling.

7. The sensor system of claim 5, wherein:
one or more substantially identical sensors have a coating with a substantially different mass capture response to serve as a reference resonator wherein a chemical detection signal is primarily the difference between an active resonator frequency or period shift and a reference resonator frequency or period shift.

8. The sensor system of claim 5, utilizing heating of the motional masses to slowly raise the temperature of a chemical sensing element containing a concentrated sample above the dew point while resonating at its resonant frequency to detect evaporating chemical mass based upon its vapor pressure as a function of temperature.

9. The sensor system of claim 1, wherein the motional mass comprises a large portion of porous silicon to achieve high surface area to mass ratio.

10. The sensing system of claim 1, further including a magnetic field substantially orthogonal to the one or more conductive traces and a vector of resonant motion to provide drive force to sustain resonant amplitude by running current through each conductive trace, in which the magnetic field comprises a permanent magnet magnetized through its thickness with one polarity backed by a highly permeable flux material which enhances the flux density at the sensor, both of which are in close proximity to the sensor with the magnet facing the sensor on one side with a small air gap and having a first dimension essentially parallel to the plane of the sensor and a second dimension extending sufficiently far to expose the conductive traces to the magnetic field such that the flux return path after the flux passes through the sensor does not require another magnet.

11. A system for sensing one or more target chemical compounds, comprising:
an array of one or more resonant sensors each comprising:
a mechanical spring-mass system employing:
a thin planar structure lying in a plane and having a damped natural frequency and comprising:
a motional mass comprising two motional masses spaced apart and dynamically linearly balanced along an X-axis in the plane, wherein two or more spring suspension elements extend in a Y-axis in the plane from the masses to a surrounding frame, the spring suspension elements having a cross-sectional geometry that results in substantially higher stiffness to out of plane motion than X-axis motion to constrain the masses to substantially linear resonant motion in the plane of the thin planar structure while minimizing motion out of the plane; and
an active coating on or in the motional mass with an affinity to capturing or reacting with the target chemical compound in order to change its own mass in response to the presence of the target chemical compound and affect a change in the damped natural frequency of the thin planar structure;
a linkage constraining the two dynamically-balanced motional masses to move 180 degrees out of phase with each other along the X-axis and substantially constraining both masses from moving side-to-side together, wherein the linkage comprises flexible beams that connect both to the frame and to each motional mass, and wherein the flexible beams define an elongated diamond shape having a first pair of opposite apexes connected to the motional masses along the X-axis and a second pair of opposite apexes connected to the frame and spaced apart farther than the first pair;
drive electronics to control the amplitude of the driven resonant mode of each sensor in the array at its damped natural frequency;
an electromagnetic drive and velocity sensor comprising one or more conductive traces across the motional mass oriented substantially orthogonal to a driven resonant motion;
a magnetic field substantially orthogonal to the one or more conductive traces and a vector of resonant motion to provide drive force to sustain resonant amplitude by running current through each conductive trace, and
one or more separate conductive traces on the motional mass that are substantially orthogonal to the vector of resonant motion to measure back EMF signals for velocity detection.

12. The sensing system of claim 11, in which sensor motion is controlled closed-loop by providing drive signals that are phase and frequency coherent to synchronously drive signals that control a desired amplitude of motion at resonance, and wherein a means of driving the signals closed loop are by waveform width modulation.

13. The sensing system of claim 11, in which sensor motion is controlled closed loop by providing drive signals that are phase and frequency coherent to synchronously drive signals that control a desired amplitude of motion at resonance, and wherein a means of driving the signals closed loop are by pulse width modulation.

14. The sensing system of claim 11, in which a sensor drive is in closed-loop-control, a waveform width control off command leaves a sensor drive loop electrically open so as to not produce current losses from back EMF related loss paths.

15. The sensing system of claim 11, in which a peak back EMF which is compensated for sensor frequency and temperature effects is compared with a desired peak back EMF and the difference is used to form an error signal for control in a processing element, and the error signal is processed by a controller to form a correction signal, and an error signal command is adjusted to maintain a desired sensor displacement.

16. The sensing system of claim 11, in which a sensor initial motion is excited by a sweep frequency forcing function;
the system further including a sensing subsystem by which a synchronous motion is detected including a combination of sensor back EMF for velocity measurement and period counting for discrimination that a resonance period has been detected.

17. The sensing system of claim 11, wherein the resonant amplitude has been established and an amplitude sensing is measured during cycles wherein a drive current is disabled.

18. The sensing system of claim 11, wherein the drive current is disabled in the regions of the cycle near zero amplitude to reduce the noise in the velocity signal.

19. The sensing system of claim 11, in which sensor frequency is measured by electronics which amplify the essentially sinusoidal back EMF velocity signal and utilizes a comparator to convert to a square waveform for frequency or period measurement using the number of counts of a high frequency reference clock.

20. The sensing system of claim 11, in which an analog-to-digital convertor is used to sample back EMFs of multiple sensors in an array and provide a sample to a processing element, the processing element utilizing a digital phase-locked-loop establishes the critical timing information from comparator inputs to determine when in the sample the peak value is to occur.

21. The sensing system of claim 11, in which sensor frequency is measured by electronics which amplifies an essentially sinusoidal back EMF velocity signal and rectifies the signal to measure velocity.

22. The sensing system of claim 11, in which sensor frequency is measured by electronics which amplifies an essentially sinusoidal back EMF velocity signal and detects the peak velocity with a peak detector.

23. The sensing system of claim 11, in which the magnetic field comprises a permanent magnet magnetized through its thickness with one polarity backed by a highly permeable flux material which enhances the flux density at the sensor, both of which are in close proximity to the sensor with the magnet facing the sensor on one side with a small air gap and having a first dimension essentially parallel to the plane of the sensor and a second dimension extending sufficiently far to expose the conductive traces to the magnetic field such that the flux return path after the flux passes through the sensor does not require another magnet.

* * * * *